US011414498B2

(12) United States Patent
Harris et al.

(10) Patent No.: US 11,414,498 B2
(45) Date of Patent: Aug. 16, 2022

(54) COMPOSITION COMPRISING ANTIBODY THAT BINDS TO DOMAIN II OF HER2 AND ACIDIC VARIANTS THEREOF

(71) Applicant: Genentech, Inc., South San Francisco, CA (US)

(72) Inventors: Reed J Harris, San Mateo, CA (US); Paul A. Motchnick, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 694 days.

(21) Appl. No.: 16/503,364

(22) Filed: Jul. 3, 2019

(65) Prior Publication Data
US 2019/0322761 A1 Oct. 24, 2019

Related U.S. Application Data

(60) Division of application No. 15/450,509, filed on Mar. 6, 2017, now abandoned, which is a continuation of application No. 14/162,255, filed on Jan. 23, 2014, now abandoned, which is a division of application No. 12/361,180, filed on Jan. 28, 2009, now Pat. No. 8,652,474.

(60) Provisional application No. 61/024,825, filed on Jan. 30, 2008.

(51) Int. Cl.
*C07K 16/32* (2006.01)
*C07K 16/06* (2006.01)
*C07K 1/18* (2006.01)
*C07K 16/28* (2006.01)
*G01N 27/447* (2006.01)
*G01N 30/02* (2006.01)
*A61K 39/00* (2006.01)

(52) U.S. Cl.
CPC .......... *C07K 16/32* (2013.01); *C07K 1/18* (2013.01); *C07K 16/065* (2013.01); *C07K 16/2863* (2013.01); *C07K 16/2896* (2013.01); *A61K 2039/505* (2013.01); *C07K 2317/24* (2013.01); *C07K 2317/41* (2013.01); *C07K 2317/76* (2013.01); *G01N 27/447* (2013.01); *G01N 30/02* (2013.01); *G01N 2030/027* (2013.01)

(58) Field of Classification Search
CPC ........ C07K 16/32; C07K 1/18; C07K 16/065; C07K 16/2863; G01N 27/447; G01N 30/02; G01N 2030/027
See application file for complete search history.

(56) References Cited

U.S. PATENT DOCUMENTS

| | | |
|---|---|---|
| 4,968,603 A | 11/1990 | Slamon et al. |
| 5,183,884 A | 2/1993 | Kraus et al. |
| 5,470,954 A | 11/1995 | Neslund et al. |
| 5,480,968 A | 1/1996 | Kraus et al. |
| 5,641,869 A | 6/1997 | Vandlen et al. |
| 5,648,237 A | 7/1997 | Carter |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,821,337 A | 10/1998 | Carter et al. |
| 5,824,311 A | 10/1998 | Greene et al. |
| 6,015,567 A | 1/2000 | Hudziak et al. |
| 6,054,297 A | 4/2000 | Carter et al. |
| 6,127,526 A | 10/2000 | Blank et al. |
| 6,165,464 A | 12/2000 | Hudziak et al. |
| 6,267,958 B1 | 7/2001 | Andya et al. |
| 6,333,169 B1 | 12/2001 | Hudziak et al. |
| 6,333,398 B1 | 12/2001 | Blank |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,417,335 B1 | 7/2002 | Basey et al. |
| 6,489,447 B1 | 12/2002 | Basey et al. |
| 6,573,043 B1 | 6/2003 | Cohen et al. |
| 6,627,196 B1 | 9/2003 | Baughman et al. |
| 6,632,979 B2 | 10/2003 | Erickson et al. |
| 6,639,055 B1 | 10/2003 | Carter et al. |
| 6,685,940 B2 | 2/2004 | Andya et al. |
| 6,719,971 B1 | 4/2004 | Carter et al. |
| 6,797,814 B2 | 9/2004 | Blank |
| 6,800,738 B1 | 10/2004 | Carter et al. |
| 6,821,515 B1 | 11/2004 | Cleland et al. |
| 6,905,830 B2 | 6/2005 | Cohen et al. |
| 6,949,245 B1 | 9/2005 | Sliwkowski |

(Continued)

FOREIGN PATENT DOCUMENTS

| | | |
|---|---|---|
| EP | 0 599 274 A1 | 11/1993 |
| EP | 1308455 A2 | 5/2003 |

(Continued)

OTHER PUBLICATIONS

Andya et al., "Mechanisms of aggregate formation and carbohydrate excipient stabilization of lyophilized humanized monoclonal antibody formulations" AAPA PharmSci (Article 10 (http://www.pharmsci.org)) 5(2):94-104 (2003).

(Continued)

*Primary Examiner* — Ruixiang Li
(74) *Attorney, Agent, or Firm* — Wendy M. Lee

(57) ABSTRACT

A composition comprising a main species HER2 antibody that binds to domain II of HER2 and acidic variants thereof is described. Pharmaceutical formulations comprising the composition, and therapeutic uses for the composition are also disclosed.

31 Claims, 16 Drawing Sheets
Specification includes a Sequence Listing.

(56) References Cited

U.S. PATENT DOCUMENTS

| | | |
|---|---|---|
| 6,984,494 B2 | 1/2006 | Ralph |
| 7,018,809 B1 | 3/2006 | Carter |
| 7,041,292 B1 | 5/2006 | Sliwkowski |
| 7,060,268 B2 | 6/2006 | Andya et al. |
| 7,074,404 B2 | 7/2006 | Basey et al. |
| 7,097,840 B2 | 8/2006 | Erickson et al. |
| 7,129,051 B2 | 10/2006 | Cohen et al. |
| 7,279,287 B2 | 10/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 2/2009 | Adams et al. |
| 7,485,704 B2 | 2/2009 | Fahrner et al. |
| 7,498,030 B2 | 3/2009 | Adams et al. |
| 7,501,122 B2 | 3/2009 | Adams et al. |
| 7,531,645 B2 | 5/2009 | Basey et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,674,589 B2 | 3/2010 | Cohen et al. |
| 7,682,609 B2 | 3/2010 | Andya et al. |
| 7,700,299 B2 | 4/2010 | Moecks et al. |
| 7,807,799 B2 | 10/2010 | Fahrner et al. |
| 7,811,773 B2 | 10/2010 | Ralph |
| 7,846,441 B1 | 12/2010 | Hellmann |
| 7,850,966 B2 | 12/2010 | Lowman et al. |
| 7,862,817 B2 | 1/2011 | Adams et al. |
| 7,879,325 B2 | 2/2011 | Kao et al. |
| 7,892,549 B2 | 2/2011 | Paton et al. |
| 7,919,254 B2 | 4/2011 | Cohen et al. |
| 7,981,418 B2 | 7/2011 | Amler et al. |
| 7,993,834 B2 | 8/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus |
| 8,337,856 B2 | 12/2012 | Blattler et al. |
| 8,372,396 B2 | 2/2013 | Andya et al. |
| 8,404,234 B2 | 3/2013 | Allison et al. |
| 8,425,908 B2 | 4/2013 | Hellmann |
| 8,440,402 B2 | 5/2013 | Mass |
| 8,529,901 B2 | 9/2013 | Hasmann et al. |
| 8,574,869 B2 | 11/2013 | Kao et al. |
| 8,591,897 B2 | 11/2013 | Bryant |
| 8,592,152 B2 | 11/2013 | Mass |
| 8,597,654 B2 | 12/2013 | Bryant |
| 8,604,014 B2 | 12/2013 | Belvin et al. |
| 8,642,036 B2 | 2/2014 | Hellmann |
| 8,652,474 B2 | 2/2014 | Harris et al. |
| 8,652,479 B2 | 2/2014 | Ebens, Jr. et al. |
| 8,663,643 B2 | 3/2014 | Berry et al. |
| 8,691,232 B2 | 4/2014 | Derynck et al. |
| 8,710,196 B2 | 4/2014 | Emery et al. |
| 8,758,747 B2 | 6/2014 | Kallmeyer et al. |
| 8,840,896 B2 | 9/2014 | Lowman et al. |
| 8,940,302 B2 | 1/2015 | Amler et al. |
| 9,017,671 B2 | 4/2015 | Andya et al. |
| 9,090,700 B2 | 7/2015 | Friess et al. |
| 9,107,926 B2 | 8/2015 | Belvin et al. |
| 9,180,185 B2 | 11/2015 | Bauss et al. |
| 9,180,189 B2 | 11/2015 | Andya et al. |
| 9,181,346 B2 | 11/2015 | Harris et al. |
| 9,249,218 B2 | 2/2016 | Basey et al. |
| 9,283,273 B2 | 3/2016 | Andya et al. |
| 9,345,661 B2 | 5/2016 | Adler et al. |
| 9,376,715 B2 | 6/2016 | Brophy et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,896,478 B2 | 2/2018 | Lebreton et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,385,405 B2 | 8/2019 | Lee-Hoeflich et al. |
| 10,501,491 B2 | 12/2019 | Emery et al. |
| 10,689,457 B2 | 6/2020 | Paton et al. |
| 10,759,866 B2 | 9/2020 | Kao et al. |
| 10,808,037 B1 | 10/2020 | Kao et al. |
| 10,849,849 B2 | 12/2020 | Eng-Wong et al. |
| 10,906,986 B2 | 2/2021 | Kao et al. |
| 11,077,189 B2 | 8/2021 | Benyunes et al. |
| 11,078,294 B2 | 8/2021 | Kao et al. |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0064785 A1 | 5/2002 | Mass |
| 2002/0090662 A1 | 7/2002 | Ralph |
| 2003/0078388 A1 | 4/2003 | Basey et al. |
| 2003/0086924 A1 | 5/2003 | Sliwkowski |
| 2003/0134344 A1 | 7/2003 | Mass |
| 2003/0147884 A1 | 8/2003 | Paton et al. |
| 2003/0152987 A1 | 8/2003 | Cohen et al. |
| 2003/0162796 A1 | 8/2003 | Hilberg et al. |
| 2003/0170234 A1 | 9/2003 | Hellmann |
| 2003/0170235 A1 | 9/2003 | Cohen |
| 2003/0202972 A1 | 10/2003 | Andya et al. |
| 2004/0013667 A1 | 1/2004 | Kelsey et al. |
| 2004/0037823 A9 | 2/2004 | Paton et al. |
| 2004/0082047 A1 | 4/2004 | Emery et al. |
| 2004/0106161 A1 | 6/2004 | Bossenmaier et al. |
| 2004/0106180 A1 | 6/2004 | Bank |
| 2004/0258685 A1 | 12/2004 | Brunetta et al. |
| 2005/0002928 A1 | 1/2005 | Hellmann |
| 2005/0025753 A1 | 2/2005 | Han et al. |
| 2005/0063972 A1 | 3/2005 | Basey et al. |
| 2005/0100944 A1 | 5/2005 | Cohen et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0099201 A1 | 5/2006 | Andya et al. |
| 2006/0121044 A1 | 6/2006 | Amler et al. |
| 2006/0165702 A1 | 7/2006 | Allison et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0216285 A1 | 9/2006 | Adams et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass |
| 2007/0184055 A1 | 8/2007 | Sliwkowski |
| 2007/0202516 A1 | 8/2007 | Mass |

(56) References Cited

U.S. PATENT DOCUMENTS

| | | |
|---|---|---|
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0102069 A1 | 5/2008 | Friess et al. |
| 2008/0108096 A1 | 5/2008 | Ralph |
| 2008/0112957 A1 | 5/2008 | Fendly et al. |
| 2008/0112958 A1 | 5/2008 | Mass |
| 2008/0160026 A1 | 7/2008 | Ashkenazi et al. |
| 2008/0171040 A1 | 7/2008 | Ebens, et al. |
| 2008/0187533 A1 | 8/2008 | Hellmann |
| 2008/0226659 A1 | 9/2008 | Erickson et al. |
| 2008/0241146 A1 | 10/2008 | Ashkenazi et al. |
| 2008/0286280 A1 | 11/2008 | Kallmeyer et al. |
| 2008/0317753 A1 | 12/2008 | Amler et al. |
| 2009/0053786 A1 | 2/2009 | Kao et al. |
| 2009/0081223 A1 | 3/2009 | Allison et al. |
| 2009/0087432 A1 | 4/2009 | Sliwkowski |
| 2009/0098135 A1 | 4/2009 | Belvin et al. |
| 2009/0099344 A1 | 4/2009 | Fahrner et al. |
| 2009/0148402 A1 | 6/2009 | Brunetta et al. |
| 2009/0148435 A1 | 6/2009 | Lebreton et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0220492 A1 | 9/2009 | Basey et al. |
| 2009/0226455 A1 | 9/2009 | Filvaroff |
| 2009/0239236 A1 | 9/2009 | Mass |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0112603 A1 | 5/2010 | Moecks et al. |
| 2010/0120053 A1 | 5/2010 | Cohen et al. |
| 2010/0158899 A1 | 6/2010 | Andya et al. |
| 2010/0196363 A1 | 8/2010 | Vanhauwere et al. |
| 2010/0285010 A1 | 11/2010 | Friess et al. |
| 2010/0298156 A1 | 11/2010 | Lee-Hoeflich et al. |
| 2011/0027190 A1 | 2/2011 | Hasmann et al. |
| 2011/0033460 A1 | 2/2011 | Fendly et al. |
| 2011/0044977 A1 | 2/2011 | Adler et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0151454 A1 | 6/2011 | Lee-Hoeflich et al. |
| 2011/0159014 A1 | 6/2011 | Lowman et al. |
| 2011/0165157 A1 | 7/2011 | Derynck et al. |
| 2011/0223159 A1 | 9/2011 | Friess et al. |
| 2011/0223619 A1 | 9/2011 | Belvin et al. |
| 2011/0236383 A1 | 9/2011 | Andya et al. |
| 2011/0245103 A1 | 10/2011 | Amler et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |
| 2012/0065381 A1 | 3/2012 | Emery et al. |
| 2012/0093838 A1 | 4/2012 | Mass |
| 2012/0107302 A1 | 5/2012 | Berry et al. |
| 2012/0107391 A1 | 5/2012 | Kelsey |
| 2012/0121586 A1 | 5/2012 | Kiermaier et al. |
| 2012/0251530 A1 | 10/2012 | Sliwkowski et al. |
| 2013/0039909 A1 | 2/2013 | Amler et al. |
| 2013/0071384 A1 | 3/2013 | Andya et al. |
| 2013/0095172 A1 | 4/2013 | Alavattam et al. |
| 2013/0108620 A1 | 5/2013 | Blattler et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0195845 A1 | 8/2013 | Fendly et al. |
| 2013/0195851 A1 | 8/2013 | Alavattam et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0323180 A1 | 12/2013 | Hasmann et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 4/2014 | Dobosz et al. |
| 2014/0128575 A1 | 5/2014 | Kao et al. |
| 2014/0128580 A1 | 5/2014 | Ebens, Jr. et al. |
| 2014/0140993 A1 | 5/2014 | Ross et al. |
| 2014/0186343 A1 | 7/2014 | Harris et al. |
| 2014/0186347 A1 | 7/2014 | Derynck et al. |
| 2014/0186867 A1 | 7/2014 | Harris et al. |
| 2014/0212411 A1 | 7/2014 | Blattler et al. |
| 2014/0227255 A1 | 8/2014 | Bauss et al. |
| 2014/0248274 A1 | 9/2014 | Kallmeyer et al. |
| 2014/0248609 A1 | 9/2014 | Mass |
| 2014/0308277 A1 | 10/2014 | Gennaro et al. |
| 2014/0322202 A1 | 10/2014 | Cohen |
| 2014/0341886 A1 | 11/2014 | Hellmann |
| 2015/0037332 A1 | 2/2015 | Paton et al. |
| 2015/0086545 A1 | 3/2015 | Sliwkowski et al. |
| 2015/0093381 A1 | 4/2015 | Allison et al. |
| 2015/0110816 A1 | 4/2015 | Blattler et al. |
| 2015/0111211 A1 | 4/2015 | Amler et al. |
| 2015/0150970 A1 | 6/2015 | Mass |
| 2015/0196642 A1 | 7/2015 | Andya et al. |
| 2015/0239969 A1 | 8/2015 | Friess et al. |
| 2015/0252113 A1 | 9/2015 | Fendly et al. |
| 2015/0273059 A1 | 10/2015 | Derynck et al. |
| 2015/0283238 A1 | 10/2015 | Friess et al. |
| 2016/0060353 A1 | 3/2016 | Lowman et al. |
| 2016/0159912 A1 | 6/2016 | Bauss et al. |
| 2016/0175438 A1 | 6/2016 | Alavattam et al. |
| 2016/0376377 A1 | 12/2016 | Basey et al. |
| 2017/0008971 A1 | 1/2017 | Dennis et al. |
| 2017/0029527 A1 | 2/2017 | Paton et al. |
| 2017/0035907 A1 | 2/2017 | Green et al. |
| 2017/0037147 A1 | 2/2017 | Allison et al. |
| 2017/0073777 A1 | 3/2017 | Lee-Hoeflich et al. |
| 2017/0106097 A1 | 4/2017 | Blattler et al. |
| 2017/0136026 A1 | 5/2017 | Sliwkowski et al. |
| 2017/0166656 A1 | 6/2017 | Lowman et al. |
| 2017/0174785 A1 | 6/2017 | Harris et al. |
| 2017/0190786 A1 | 7/2017 | Fendly et al. |
| 2017/0226224 A1 | 8/2017 | Basey et al. |
| 2017/0313780 A1 | 11/2017 | Kao et al. |
| 2017/0360928 A1 | 12/2017 | Mass |
| 2018/0037622 A1 | 2/2018 | Gennaro et al. |
| 2018/0037660 A1 | 2/2018 | Gennaro et al. |
| 2018/0037661 A1 | 2/2018 | Gennaro et al. |
| 2018/0118781 A1 | 5/2018 | Lebreton et al. |
| 2018/0134803 A1 | 5/2018 | Douthwaite et al. |
| 2018/0162951 A1 | 6/2018 | Cohen |
| 2018/0201692 A1 | 7/2018 | Lowman et al. |
| 2018/0221481 A1 | 8/2018 | Beattie et al. |
| 2018/0221488 A1 | 8/2018 | Andya et al. |
| 2018/0228895 A1 | 8/2018 | Adler et al. |
| 2018/0236072 A1 | 8/2018 | Derynck et al. |
| 2018/0236093 A1 | 8/2018 | Bryant |
| 2018/0244715 A1 | 8/2018 | Emery et al. |
| 2018/0250397 A1 | 9/2018 | Benyunes et al. |
| 2018/0251536 A1 | 9/2018 | Friess et al. |
| 2018/0251557 A1 | 9/2018 | Chui et al. |
| 2018/0274038 A1 | 9/2018 | Belousov et al. |
| 2018/0280408 A1 | 10/2018 | Belvin et al. |
| 2018/0282428 A1 | 10/2018 | Fendly et al. |
| 2018/0296470 A1 | 10/2018 | Eng-Wong et al. |
| 2018/0327510 A1 | 11/2018 | Allison et al. |
| 2019/0055317 A1 | 2/2019 | Baughman et al. |

(56) References Cited

U.S. PATENT DOCUMENTS

| | | |
|---|---|---|
| 2019/0070291 A1 | 3/2019 | Mass |
| 2019/0117769 A1 | 4/2019 | Benyunes et al. |
| 2019/0240185 A1 | 8/2019 | Desmond-Hellmann et al. |
| 2019/0298861 A1 | 10/2019 | Dobosz et al. |
| 2019/0322761 A1 | 10/2019 | Harris |
| 2019/0323089 A1 | 10/2019 | Lee-Hoeflich et al. |
| 2019/0345258 A1 | 11/2019 | Gennaro et al. |
| 2019/0352331 A1 | 11/2019 | Emery et al. |
| 2019/0352332 A1 | 11/2019 | Emery et al. |
| 2019/0352333 A1 | 11/2019 | Emery et al. |
| 2019/0374547 A1 | 12/2019 | Sliwkowski et al. |
| 2020/0048362 A1 | 2/2020 | Blattler et al. |
| 2020/0155701 A1 | 5/2020 | Bryant |
| 2020/0157238 A1 | 5/2020 | Gennaro et al. |
| 2020/0179515 A1 | 6/2020 | Andya et al. |
| 2020/0199690 A1 | 6/2020 | Belousov et al. |
| 2020/0206348 A1 | 7/2020 | Benyunes et al. |
| 2020/0237910 A1 | 7/2020 | Beattie et al. |
| 2020/0239595 A1 | 7/2020 | Allison et al. |
| 2020/0246267 A1 | 8/2020 | Haas et al. |
| 2020/0376120 A1 | 12/2020 | Benyunes et al. |
| 2021/0015919 A1 | 1/2021 | Benyunes et al. |
| 2021/0042016 A1 | 2/2021 | Chui et al. |
| 2021/0047429 A1 | 2/2021 | Paton et al. |
| 2021/0085597 A1 | 3/2021 | Eng-Wong et al. |
| 2021/0130398 A1 | 5/2021 | Emery et al. |
| 2021/0130399 A1 | 5/2021 | Emery et al. |
| 2021/0171571 A1 | 6/2021 | Emery et al. |
| 2021/0188993 A1 | 6/2021 | Kao et al. |
| 2021/0330789 A1 | 10/2021 | Benyunes et al. |
| 2021/0353753 A1 | 11/2021 | Adler et al. |
| 2021/0403599 A1 | 12/2021 | Badovinac-Crnjevi et al. |
| 2022/0090212 A1 | 3/2022 | Belousov et al. |

FOREIGN PATENT DOCUMENTS

| | | |
|---|---|---|
| EP | 03/068801 A2 | 8/2003 |
| WO | 94/00136 A1 | 1/1994 |
| WO | 94/22478 | 10/1994 |
| WO | 99/57134 | 11/1999 |
| WO | 01/00245 A2 | 1/2001 |
| WO | 01/00245 A3 | 1/2001 |
| WO | 2004/008099 A2 | 1/2004 |
| WO | 2004/103274 A3 | 12/2004 |
| WO | 2006/033700 A2 | 3/2006 |
| WO | 2006/044908 A2 | 4/2006 |
| WO | 2006/063042 A2 | 6/2006 |
| WO | 2006/078307 A1 | 7/2006 |
| WO | 2006/091693 A2 | 8/2006 |
| WO | 2006/096861 A2 | 9/2006 |
| WO | 2007/013950 A2 | 2/2007 |
| WO | 2007/145862 A2 | 12/2007 |
| WO | 2009/099829 A1 | 8/2009 |
| WO | 2009/117277 A2 | 9/2009 |
| WO | 2011/146568 A1 | 11/2011 |
| WO | 2011/146568 A8 | 11/2011 |
| WO | 2012/078771 A1 | 6/2012 |
| WO | 2012/120004 A1 | 9/2012 |
| WO | 2013/083810 A1 | 6/2013 |
| WO | 2014/083178 A1 | 6/2014 |
| WO | 2014/172371 A2 | 10/2014 |
| WO | 2238172 B1 | 2/2018 |
| WO | 2018/085513 A1 | 5/2018 |
| WO | 2018/125589 A1 | 7/2018 |
| WO | 2018/160654 | 9/2018 |
| WO | 2018/200505 A1 | 11/2018 |
| WO | 2022/013189 A1 | 1/2022 |

OTHER PUBLICATIONS

Catak et al., "Reaction Mechanism of Deamidation of Asparaginyl Residues in Peptides: Effect of Solvent Molecule" J. Phys. Chem 110:8354-8365 ( 2006).

"CMC Forum: Standard Reference Materials for Biopharmaceutical Products" The GoldSheet 40(6):1-20 ( 2006).

Cordoba et al., "Non-enzymatic hinge region fragmentation of antibodies in solution" J Chromatogr B 818:115-121 ( 2005).

Declaration of Dr. Karolina Peciak with CV, pp. 1-16 ( Sep. 3, 2021).

Emons et al., "New Definitions on Reference Materials" Accred Qual Assur 10:576-578 ( 2006).

Experimental data by Dr. Reddy's Labs (Opponent 4) in Opposition to European Patent No. 2238172, pp. 1-3 (2021).

FDA, "Guidance for Industry: INDs for Phase 2 and Phase 3 Studies of Drugs, Including Specified Therapeutic Biotechnology-Derived Products: Chemistry, Manufacturing, and Controls Content and Format":1-18 ( 1999).

Gibco, "A Guide to Serum-Free Cell Culture 11 Pages" (With CD-CHO-Cells 11619-02 Catalog, 2 Pages) (With Email exchange regarding CD-CHO Media, 6 Pages) ,:1-18 ( 2003).

Hutterer et al., "Monoclonal Antibody Disulfide Reduction During Manufacturing" Landes Bioscience 5(4):608-613 ( 2013).

"ICH Harmonised Tripartite Guideline Specifications: Test Procedures and Acceptance Criteria for Biotechnological/Biological Products Q6B" International Conference on Harmonisation of Technical Requirements for Registration of Pharmaceuticals for Human Use:1-20 ( 1999).

Internet Archive, Wayback Machine Website "Glycation", 2007 Wikipedia Snapshot taken from the WebArchive, http://en.wikipedia.org/wiki/glycation, pp. 1-3 (2007).

Jenkins et al., "Getting the glycosylation right: Implications for the biotechnology industry" Nature 14:975-981 ( 1996).

Kennedy et al., "Glycation of monoclonal antibodies impairs their ability to bind antigen" Clin Exp Immunol 98:245-251 ( 1994).

Kim et al., "Drifts in ADCC-related attributes of Herceptin: Impact on development of a trastuzumab biosimilar" MAbs 9(4):704-714 ( 2017).

Liu et al., "Disulfide bond structures of lgG molecules" Landes Bioscience 4(1):17-23 ( 2012).

Liu et al., "Ranking the Susceptibility of Disulfide Bonds in Human IgG1 Antibodies by Reduction, Differential Alkylation, and LC-MS Analysis"Anal Chem 82:5219-5226 ( 2010).

Ma et al., "Analysis of Protein Therapeutics by Capillary Electrophoresis" Chromatographia Supplement 53:S75-S89 ( 2001).

Peciak & Behrens "Experimental report Pertuzumab—Analysis of acidic variants AV Report: DEOB-PCC-0057" submitted by Hexal/Sandoz (Opponent 1) in Opposition to European Patent No. 2238172, pp. 1-39 Sep. 3, 2021.

Pereira Morais et al., "Analysis of protein glycation using phenylboronate acrylamide gel electrophoresis" Proteomics 10:48-58 ( 2010).

Riddles et al., "Ellman'reagent: 5,5'-dithiobis(2-nitrobenzoic acid)—a reexamination" Anal Biochem 94:75-81 ( 1979).

Robinson et al., "Prediction of primary structure deamidation rates of asparaginyl and glutaminyl peptides through steric and catalytic effects" J Peptide Res 63:437-448 ( 2004).

Saleem et al., "A chemical and computational approach to comprehensive glycation characterization on antibodies" MAbs 7(4):719-731 ( 2015).

Seward, "NBS Standard Reference Materials Catalog 1988-89" U.S. Government Printing Office:1-6 ( 1998).

Shen et al., "Gycation of RhuMAb E25" J Biomol Techniques 10(2):109 ( 1999).

Sonderegger, "Antibody Reduction and More Recent Challenges to the Scale-Up of CHO Manufacturing Processes" Wilbio 14th Waterside Conference:1-14 ( 2009).

U.S. Department of Health and Human Services, "Development of Therapeutic Protein Biosimilars: Comparative Analytical Assessment and Other Quality-Related Considerations":1-31 ( 2019).

Wang et al., "Investigation of Antibody Disulfide Reduction and Re-Oxidation and Impact to Biological Activities" Journal of Pharmaceutical and Biomedical Analysis 102:519-528 ( 2015).

Wei et al., "Glycation of antibodies: Modification, methods and potential effects on biological functions" MAbs 9(4):586-594 ( 2017).

(56) References Cited

OTHER PUBLICATIONS

Yuk et al., "Controlling glycation of recombinant antibody in fed-batch cell cultures" Biotechnol Bioeng 108(11):2600-2610 ( 2011).
Zhang et al., "Rapid Identification of Low Level Glycation Sites in Recombinant Antibodies by Isotopic Labeling with 13C6-Reducing Sugars" Anal Chem 84:2313-2320 ( 2012).
Zhang et al., "Unveiling a glycation hot spot in a recombinant humanized monoclonal antibody" Anal Chem 80:2379-2390 ( 2008).
(Summary of Facts and Submission in European Patent Application No. 09709065.8 Dated Dec. 8, 2021), 26 Pages.
Adams et al., "Humanization of a recombinant monoclonal antibody to produce a therapeutic HER dimerization inhibitor, pertuzumab" Cancer Immunol Immunother. 55(6):717-727 ( 2006).
Annex A Technical Background and Common General Knowledge of the Skilled Person Submitted by Konig, Szynka, Tilmann, Von Renesse in Opposition Against European Patent No. 3401335 dated Mar. 30, 2022, 35 Pages.
Annex B Discussion of the Experimental Data Submitted by Konig, Szynka, Tilmann, Von Renesse in Opposition Against European Patent No. 3401335 dated Mar. 30, 2022, 29 Pages.
Chen et al., "Excerpt of CE in Biotechnology: Practical Applications for Protein and Peptide Analyses":1-2 ( 2020).
Chu, "Accumulation of Succinimide in a Recombinant Monoclonal Antibody in Mildly Acidic Buffers Under Elevated Temperatures" Pharm Res 24(6):1145-1156 ( 2007).
Decision Revoking European Patent 2238172 Dated Dec. 8, 2021, 55 Pages.
Dillon et al., "Structural and functional characterization of disulfide isoforms of the human IgG subclass" J Biol Chem 283(23):16206-16215 (Jun. 6, 2008).
Examiner Communication dated Nov. 19, 2020 in European Patent Application No. 18157419.5, 3 Pages.
Gibco, "A Guide to Serum-Free Cell Culture" (With Annex),:1-19 ( 2003).
Jenkins et al., "Getting the glycosylation right: Implications for the biotechnology industry" Nature Biotechnol 14:975-981 (Aug. 1996).
Petrosyan et al., "Lectin-Enzyme Assay as a Method of Estimation of Immunoglobulins' Glycosylation" Ukrainian Biochemical Journal (With English Abstract Translation), 78(4):125-133.
Proprietor's Submission Dated Aug. 29, 2019 in European Patent Application No. 18157419.5, 5 Pages.
Santora et al., "Characterization of Maleuric Acid Derivatives on Transgenic Human Monoclonal Antibody Due to Post-Secretional Modifications in Goat Milk" Biomed Chromatogr 20:843-856 ( 2006).
Santora et al., "Characterization of Recombinant Human Monoclonal Tissue Necrosis Factor-a Antibody Using Cation-Exchange HPLC and Capillary Isoelectric Focusing" Anal Biochem 275:98-108 ( 1999).
Wypych et al., "Human IgG2 Antibodies Display Disulfide-Mediated Structural Isofroms" J Biol Chem 283(23):16194-16205 ( 2008).
Zhang et al., "Separation and Characterization of a Monoclonal IgG Antibody by Cation Exchange Chromatography" Bioprocess Journal 2(6):37-43 ( 2003).
(Porter, Jill, the role of Analytical Comparability in the Global Approval of Zenapax, Case Studies—Biotech Manufacturing Changes, Slides 1-18, The 3rd International Conference: Strategic Use of Comparability Studies and Assays for Well Characterized Biologicals, Washington D.C., Sep. 18-21, 2000).
(Reid et al., Effects of Cell Culture Process Change on Humanized Characteristics, Poster presented at WCBP 2003 conference in San Francisco, Jan. 7-10, 2003, p. 1).
"Appendix A" attached to Opposition filed Nov. 20, 2018 by Hans Ulrich Dorries against EP 2 238 172 ("Opponent 2"), describing experiments performed on behalf of Opponent 2, pp. 1-3.
"Appendix B" attached to Opposition filed Nov. 20, 2018 by Hans Ulrich Dorries against EP 2 238 172 ("Opponent 2"), describing experiments performed on behalf of Opponent 2, pp. 1-5.
"Appendix C" attached to Opposition filed Nov. 20, 2018 by Hans Ulrich Dorries against EP 2 238 172 ("Opponent 2"), describing experiments performed on behalf of Opponent 2, pp. 1-2.
Aasland et al., "Expression of Oncogenes in Thyroid Tumours: Coexpression of c-erbB2/neu and c-erbB" Brit J Cancer 57(4):358-363 ( 1988).
Agus et al. et al., "Phase I clinical study of pertuzumab, a novel HER dimerization inhibitor, in patients with advanced cancer" J Clin Oncol 23(11):2534-2543 (Apr. 10, 2005).
Agus et al., "Clinical Activity in a Phase I Trial of HER-2-Targeted rhuMAb 2C4 (pertuzumab) in Patients with Advanced Solid Malignancies (AST)" Proceedings of the American Society of Clinical Oncology (Abstract No. 771), 22:192 ( 2003).
Agus, David B. et al. et al., "Phase I clinical study of pertuzumab, a novel HER dimerization inhibitor, in patients with advanced cancer" J Clin Oncol 23(11):2534-2543 (Apr. 10, 2005).
Arteaga, C. L. et al., "p185\\\superscript:c-erbB-2\\\ Signaling Enhances Cisplatin-induced Cytotoxicity in Human Breast Carcinoma Cells: Association Between an Oncogenic Receptor Tyrosine Kinase and Drug-induced DNA Repair" Cancer Res 54(14):3758-3765 (Jul. 15, 1994).
Bacus, S. S. et al., "Differentiation of Cultured Human Breast Cancer Cells (AU-565 and MCF-7) Associated With Loss of Cell Surface HER-2/neu Antigen" Mol Carcinogen 3(6):350-362 ( 1990).
Bacus, S. S. et al., "Tumor-inhibitory Monoclonal Antibodies to the HER-2/Neu Receptor Induce Differentiation of Human Breast Cancer Cells" Cancer Res 52(9):2580-2589 (May 1, 1992).
Beselga and Mendelsohn et al., "Receptor Blockade With Monoclonal Antibodies As Anti-Cancer Therapy" Pharmac Ther 64:127-154 ( 1994).
Baselga et al., "Objective response rate in a phase II multicenter trial of pertuzumab (P), a HER2 dimerization inhibiting monoclonal antibody, in combination with trastuzumab (T) in patients (pts) with HER2-positive metastatic breast cancer (MBS) which has progressed during treatment with T" J Clin Oncol (Abstract 1004; 2007 ASCO Annual Meeting), 25(18S Suppl Jun. 20):1-2 ( 2007).
Baselga et al., "Phase II Study of Weekly Intravenous Recombinant Humanized Anti-p185\\\superscript:HER2\\\ Monoclonal Antibody in Patients With HER2/neu-Overexpressing Metastatic Breast Cancer" J Clin Oncol 14(3):737-744 (Mar. 1996).
Beckman et al., "Antibody Constructs in Cancer Therapy" Cancer 109(2):170-179 (Jan 15, 2007).
Biotechnology Industry Organization, Dkt. No. 2004N-0355, Scientific Considerations Related to Developing Follow-on Protein Products, Dec. 13, 2004, pp. 1-39.
Borst et al., "Oncogene Alterations in Endometrial Carcinoma" Gynecol Oncol 38(3):364-366 (Sep. 1990).
Boswell et al., "Effects of Charge on Antibody Tissue Distribution and Pharmacokinetics" Bioconjugate Chem. 21:2153-2163 ( 2010).
Bumbaca et al., "Physiochemical and Biochemical Factors Influencing the Pharmacokinetics of Antibody Therapeutics" The AAPS Journal 14(3):554-558 (Sep. 2012).
Carraway and Cantley, "A Neu Acquaintance for ErbB3 and ErbB4: a Role for Receptor Heterodimerization in Growth Signaling" Cell 78:5-8 (Jul. 15, 1994).
Carraway et al., "Neuregulin-2, A New Ligand of ErbB3/ErbB4-Receptor Tyrosine Kinases" Nature 387:512-516 (May 29, 1997).
Chaderjian et al., "Effect of Copper Sulfate on Performance of a Serum-Free CHO Cell Culture Process and the Level of Free Thiol in the Recombinant Antibody Expressed" Biotechnology Progress 21(2):550-553 ( 2005).
Chang et al. et al., "Ligands for ErbB-Family Receptors Encoded by a Neuregulin-Like Gene" Nature 387:509-512 (May 29, 1997).
Chirino, A. J., et al., "Characterizing biological products and assessing" Nat Biotechnol 22(11):1383-1391 (Nov 4, 2004).
Cohen et al., "Expression Pattern of the neu (NGL) Gene-Encoded Growth Factor Receptor Protein (p185\\\superscript:neu\\\) in Normal and Transformed Epithelial Tissues of the Digestive Tract" Oncogene 4(1):81-88 (Jan. 1989).
Cohen et al., "β-Elimination and Peptide Bond Hydrolysis: Two Distinct Mechanisms of Human IgG1 Hinge Fragmentation upon Storage" Journal of the American Chemical Society 129:6976-6977 ( 2007).

(56) References Cited

OTHER PUBLICATIONS

Cromwell, M., et al., "Protein Aggregation and Bioprocessing" AAPS Journal 8(3):E572-E579 (Sep 15, 2006).
Declaration of Dr. John T. Stults re: WO 2009/099829, signed Sep. 8, 2014, pp. 1-5.
Declaration of Dr. Sateesh Kumar Nataraian, Ph.D., Vice President, Dr. Reddy's Laboratories Limited, Re: European Patent No. EP 2 238 172 B1, Nov. 19, 2018, pp. 1-8.
Declaration of Dr. Yung-Hsiang Kao, pp. 1-6 ( May 29, 2019).
Declaration of Reed Harris re: European Application No. 09 709 065.8, dated Aug. 24, 2017 (2 pgs.).
Declaration/Statement of Luisa Fernanda Diaz Pinula, re: Colombian counterpart of WO 2009/099829, signed Sep. 29, 2014, pp. 1-5.
Dionex Product Manual for ProPac WCX-10 and ProPac SCX-10. Document No. 031410-17., pp. 1-30 (Feb. 2007).
Drebin et al., "Down-Modulation of an Oncogene Protein Product and Reversion of the Transformed Phenotype by Monoclonal Antibodies" Cell 41(3):695-706 (Jul. 1985).
Drebin et al., "Monoclonal Antibodies Reactive With Distinct Domains of the neu Oncogene-Encoded p185 Molecule Exert Synergistic Anti-Tumor Effects In Vivo" Oncogene 2:273-277 ( 1988).
D'Souza and Taylor-Papadimitriou, "Overexpression of ERBB2 in human mammary epithelial cells signals inhibition of transcription of the E-cadherin gene" P Natl Acad Sci USA 91(15):7202-7206 (Jul. 1994).
Earp et al., "Heterodimerization and Functional Interaction Between EGF Receptor Family Members: A New Signaling Paradigm With Implications For Breast Cancer Research" Breast Cancer Res Treatment 35:115-132 ( 1995).
EMA Raptiva, Scientific Discussion, Jan. 1, 2004, pp. 1-37.
EMBOSS Needle—Alignment, www.ebi.ac.uk, Seq ID No. 15, Nov. 16, 2018, pp. 1-3.
EMBOSS Needle—Assignment, www.ebi.ac.uk, Seq. ID 16, Nov. 16, 2018, pp. 1-6.
Extract from 2007 IND 9900 Amendment, rhuMAb 2C4 (Pertuzumab), Sep. 26, 2007, pp. 1-5 (Extract: BB-IND 9900 rhuMAb 2C4 (Pertuzumab) Information Amendment).
Fahrner et al., "Industrial Purification of Pharmaceutical Antibodies: Development, Operation, and Validation of Chromatography Processes" Biotechnol Genet Eng 18:301-327 ( 2001).
Fendly et al., "Characterization of murine monoclonal antibodies reactive to either the human epidermal growth factor receptor or HER2/neu gene product" Cancer Res 50:1550-1558 (Mar. 1, 1990).
Franklin et al., "Insights into ErbB signaling from the structure of the ErbB2-pertuzumab complex" Cancer Cell 5:317-328 (Apr. 2004).
Fukushige et al., "Localization of a Novel v-erbB-Related Gene, c-erbB-2, on Human Chromosome 17 and Its Amplification in a Gastric Cancer Cell Line" Mol Cell Biol 6(3):955-958 (Mar. 1986).
Genentech, Inc., 'Genentech reports additional data from biooncology pipeline at ASCO' (press release), pp. 1-2 ( Jun. 1, 2003).
Gevondyan, N.M., et al., "Four Free Cysteine Residues Found Human IgG1 of Healthy Donors" Biochemistry (Moscow) 71(3):279-284 (Nov. 27, 2005).
Graham, "Product-Related Impurities and their Impact on Product Quality/Safety: An FDA Perspective and Recommendations" Slides pp. 35.
Groenen et al., "Structure-Function Relationships for the EGT/TGF-α Family of Mitogens" Growth Factors 11:235-257 ( 1994).
Gu et al., "Overexpression of her-2/neu in Human Prostate Cancer and Benign Hyperplasia" Cancer Lett 99:185-189 ( 1996).
Guerin et al., "Overexpression of Either c-myc or c-erbB-2/neu Proto-oncogenes in Human Breast Carcinomas: Correlation with Poor Prognosis" Oncogene Res 3(1):21-31 ( 1988).
Hancock, M. C. et al., "A Monoclonal Antibody Against the c-erbB-2 Protein Enhances the Cytotoxicity of cis-Diamminedichloroplatinum Against Breast and Ovarian Tumor Cell Lines" Cancer Res 51:4575-4580 (Sep. 1, 1991).

Harari et al., "Neuregulin-4: A Novel Growth Factor That Acts Through the ErbB-4 Receptor Tyrosine Kinase" Oncogene 18:2681-2689 ( 1999).
Harris, "Free Thiol Issues in the Production of a Recombinant Antibody" Slides Waterside Conference, pp. 14 (2001).
Harris, "Heterogeneity of recombinant antibodies: linking structure to function" Dev Biol (Basel). 122:117-127 ( 2005).
Harris, R. J. et al. et al., "Identification of multiple sources of charge heterogeneity in a recombinant antibody" J Chromatogr B 752:233-245 ( 2001).
Harris, R., "Chromatographic Techniques for the Characterization of Human Monoclonal Antibodies: rhuMAb HER2" (Abstracts and Slides) The Waterside Monoclonal Conference, Norfolk, Virginia—US, pp. 1-7 ( Apr. 22, 1996).
Harris, R.J., "Processing of C-terminal lysine and arginine residues of proteins isolated from mammalian cell culture" Journal of Chromatography A 705:129-134 ( 1995).
Harris, Reed J. et al. Mass Spectrometry in the Biological Sciences "Identifying Unexpected Protein Modifications" (Mass Spectrometry in the Biological Sciences. Humana Press, Totowa, NJ.), Carr S.A., Burlingame::334-350 (Jan. 1996).
Harris, Reed, The Ideal Chromatographic Antibody Characterization Method, Slides 1-36, IBC Antibody Production Conference, Feb. 13, 2002.
Harwerth, I. et al., "Monoclonal Antibodies Against the Extracellular Domain of the erbB-2 Receptor Function as Partial Ligand Agonists" J Biol Chem 267(21):15160-15167 (Jul. 25, 1992).
Holmes et al., "Identification of Heregulin, A Specific Activator of p185\\\superscript:erbB2\\\" Science 256:1205-1210 (May 22, 1992).
Hudziak et al. et al., "p185\\\superscript:HER2\\\ Monoclonal Antibody Has Antiproliferative Effects In Vitro and Sensitizes Human Breast Tumor Cells to Tumor Necrosis Factor" Mol Cell Biol 9(3):1165-1172 (Mar. 1989).
Hunt et al., "Capillary electrophoresis sodium dodecyl sulfate nongel sieving analysis of a therapeutic recombinant monoclonal antibody: a biotechnology perspective" Anal Chem. 71(13):2390-7 ( 1999).
Hunt, G., et al., "Capillary isoelectric focusing and sodium dodecyl sulfate-capillary gel electrophoresis of recombinant humanized monoclonal antibody HER2" J Chromatogr 744:295-301 (Jan. 1, 1996).
Immunology by Kuby, 5th Edition "Chapter 4, Antibodies: Structure and Function":pp. 1-30 ( 2002).
Internet Archive, Wayback Machine Website, https://web.archive.org/web/2016*/http://www.emea.europa.eu/humandocs/PDFs/EPAR/raptiva/6565604en6, pp. 1-3.
Internet Archive, Wayback Machine Website, https://web.archive.org/web//20050501000000*/http://www.bio.org/reg/2041213, Oct. 6, 2019, pp. 1-3.
Kao et al., "Mechanism of Antibody Reduction in Cell Culture Production Processes" Biotechnology and Bioengineering 107(4):622-632 (Nov. 1, 2010).
Kasprzyk, P. G. et al., "Therapy of an Animal Model of Human Gastric Cancer Using a Combination of Anti-erbB-2 Monoclonal Antibodies" Cancer Res 52(10):2771-2776 (May 15, 1992).
Kern et al., "p185\\\superscript:neu\\\ Expression in Human Lung Adenocarcinomas Predicts Shortened Survival" Cancer Res 50(16):5184-5191 (Aug. 15, 1990).
Khawli et al., "Charge Variants in IgG1; Isolation, Characterization, In Vitro Binding Properties and Pharmacokinetics in Rats" Landes Bioscience 2(6):613-624 ( 2010).
Khawli et al., "Pharmacokinetic characteristics and biodistribution of radioiodinated chimeric TNT-1, -2, and -3 monoclonal antibodies after chemical modification with biotin" Cancer Biother Radiopharm 17(4):359-370 ( 2002).
King et al., "Amplification of a Novel v-erbB-Related Gene in a Human Mammary Carcinoma" Science 229:974-976 (Sep. 1985).
Klapper et al., "A Subclass of Tumor-Inhibitory Monoclonal Antibodies to ErbB-2/HER2 Blocks Crosstalk With Growth Factor Receptors" Oncogene 14:2099-2109 ( 1997).
Kobayashi et al., "The Pharmacokinetic Characteristics of Glycolated Humanized Anti-Tac Fabs are Determined by their Isoelectric Points" Cancer Research 59:422-430 (Jan. 15, 1999).

(56) References Cited

OTHER PUBLICATIONS

Kotts et al., 'Differential growth inhibition human carcinoma cells exposed to monoclonal antibodies directed against the extracellular domain of the HER2/ERBB2 protooncogene' In Vitro (Abstract #176) 26(3):59A (1990).
Kozlowski, "Perspectives on Specifications for Monoclonal Antibodies" (Division of Monoclonal Antibodies, OBP/OPS/CDER slides presented at IBC Conference (2004), pp. 1-46.).
Kozlowski, S., et al., "Current and Future Issue in the Manufacturing and Development of Monoclonal Antibodies" Adv Drug Deliver Rev 58:707-722 (May 6, 2006).
Kroon et al., "Identification of Sites of Degradation in a Therapeutic Monoclonal Antibody by Peptide Mapping" Pharmaceutical Research 9(11):1386-1393 (Apr. 1, 1992).
Kumar et al., "Regulation of phosphorylation of the c-erbB-2/HER2 gene product by a monoclonal antibody and serum growth factor(s) in human mammary carcinoma cells" Mol Cell Biol 11(2):979-986 (Feb. 1991).
Lee et al. et al., "Transforming Growth Factor α: Expression, Regulation, and Biological Activities" Pharmacol Rev 47(1):51-85 (Mar. 1995).
Lee et al., "Monoclonal Antibody Radiopharmaceuticals: Cationization, Pegylation, Radiometal Chelation, 2003) Pharmacokinetics, and Tumor" Bioconjugate Chem 14(3):546-553 (Feb. 20, 2003).
Lemke, G., "Neuregulins in Development" Molecular Cellular Neurosciences 7:247-262 ( 1996).
Levi et al., "The Influence of Heregulins on Human Schwann Cell Proliferation" J Neurosci 15(2):1329-1340 (Feb. 1995).
Lewis et al. et al., "Differential Responses of Human Tumor Cell Lines to Anti-p185\\\superscript:HER2\\\ Monoclonal Antibodies" Cancer Immunol Immunother 37:255-263 ( 1993).
Lewis et al., "Growth regulation of human breast and ovarian tumor cells by heregulin: Evidence for the requirement of ErbB2 as a critical component in mediating heregulin responsiveness" Cancer Res 56:1457-1465 (Mar. 15, 1996).
Lispi et al., "Heterogeneity of Commercial Recombinant Human Growth Hormone (r-hGH) Preparations Containing a Thioether Variant"Journal of Pharmaceutical Sciences 98(12):4511-4524 (Dec. 2009).
Liu, H. et al. et al., "Heterogeneity of monoclonal antibodies" J Pharm Sciences 97(7):2426-2447 (Jul. 2008), with Wiley Online Publication Link stating "first published," Sep. 7, 2007, (4 pages), attached thereto.
Liu, H., et al., "Characterization of lower molecular weight artifact bands of recombinant monoclonal IgG1 antibodies on non-reducing SDS-PAGE" Biotechnol Lett 29:1611-1622 (Jul. 4, 2007).
Lyrubarskaya et al., "Analysis of recombinant monoclonal antibody isoforms by electrospray ionization mass spectrometry as a strategy for streamlining characterization of recombinant monoclonal antibody charge heterogeneity" Analytical Biochemistry 348:24-39 ( 2006).
Maier, L. A. et al., "Requirements for the Internalization of a Murine Monoclonal Antibody Directed against the HER-2/neu Gene Product c-erbB-2" Cancer Res 51(19):5361-5369 (Oct. 1, 1991).
Manning et al., "Stability of Protein Pharmaceuticals" Pharm. Res. 6(11):903-918 (1989).
Masui et al. et al., "Growth Inhibition of Human Tumor Cells in Athymic Mice by Anti-Epidermal Growth Factor Receptor Monoclonal Antibodies" Cancer Res 44(3):1002-1007 (Mar. 1984).
McCann et al., "c-erbB-2 Oncoprotein Expression in Primary Human Tumors" Cancer 65(1):88-92 (Jan. 1, 1990).
McKenzie, S. J. et al., "Generation and Characterization of Monoclonal Antibodies Specific for the Human neu Oncogene Product, p185" Oncogene 4:543-548 ( 1989).
Michels et al., "Fluorescent Derivation Method of Proteins for Characterization by Capillary Electrophoresis-Sodium Dodecyl Sulfate with Laser-Induced Fluorescence Detection" Analytical Chemistry 79(15):5963-5971 (Aug. 1, 2007).

Morrissey et al., "Axon-Induced Mitogenesis of Human Schwann Cells Involves Heregulin and p185\\\superscript:erbB2\\\" P Natl Acad Sci USA 92:1431-1435 (Feb. 1995).
Myers et al., "Biological Effects of Monoclonal Antireceptor Antibodies Reactive with neu Oncogene Product, p185neu" Method Enzymol 198:277-290 ( 1991).
Nahta, R. et al., "The HER-2-targeting antibodies trastuzumab and pertuzumab synergistically inhibit the survival of breast cancer cells" Cancer Res 64(7):2343-2346 (Apr. 1, 2004).
Park et al., "Amplification, Overexpression, and Rearrangement of the erbB-2 Protooncogene in Primary Human Stomach Carcinomas" Cancer Res 49(23):6605-6609 (Dec. 1, 1989).
PERJETA® (pertuzumab) Full Prescribing Information, pp. 1-15 (revised Jun. 2012).
Perkins, M. et al. et al., "Determination of the origin of charge heterogeneity in a murine monoclonal antibody" Pharm Res 17(9):1110-1117 ( 2000).
Pietras et al., "Antibody to HER-2/neu receptor blocks DNA repair after cisplatin in human breast and ovarian cancer cells" Oncogene 9:1829-1838 ( 1994).
Plowman et al., "Heregulin induces tyrosine phosphorylation of HER4/p180\\\superscript:erbB4\\\" Nature 366:473-475 (Dec. 2, 1993).
Plowman et al., "Ligand-specific activation of HER4/p180\\\superscript:erbB4\\\, a fourth member of the epidermal growth factor receptor family" P Natl Acad Sci USA 90:1746-1750 (Mar. 1993).
Proprietor's submission of Sep. 8, 2016, in European Patent Application 09709065.8, 9 pages.
Raju et al. et al., "Species-Specific Variation in Glycosylation of IgG: Evidence for the Species-Specific Sialylation and Branch-Specific Galactosylation and Importance for Engineering Recombinant Glycoprotein Therapeutics." Glycobiology 10(5):477-486 ( 2000).
Rao, P.E., et al. Orthoclone OKT3 "Chemical Mechanisms and Functional Effects of Degradation of a Therapeutic Monoclonal Antibody" New Jersey:R.W. Johnson Pharmaceutical Research Institute,(Chap. 4):135-157 (Jan. 1, 1983).
Riddles, P.W., et al., "Reassessment of Ellman's Reagent" Method Enzymol 91:49-60 (Jan. 1, 1983).
Ross et al., "HER-2/neu Gene Amplification Status in Prostate Cancer by Fluorescence in Situ Hybridization" Hum Pathol 28(7):827-833 (Jul. 1997).
Ross et al., "Prognostic Significance of HER-2/neu Gene Amplification Status by Fluorescence In Situ Hybridization of Prostate Carcinoma"Cancer 79(11):2162-2170 (Jun. 1, 1997).
Sadasivan et al., "Overexpression of Her-2/Neu May Be An Indicator of Poor Prognosis in Prostate Cancer" J Urol 150:126-131 (Jul. 1993).
Salas-Solano et al., "Optimization and Validation of a Quantitative Capillary Electrophoresis Sodium Dodecyl Sulfate Method for Quality Control and Stability Monitoring of Monoclonal Antibodies" Analytical Chemistry 78(18):6583-94 ( 2006).
Salas-Solano, O., et al. Capillary Electrophoresis Methods for Pharmaceutical Analysis "Capillary Electrophoresis and Bioanalysis" Ahuja, Satinder, London, England—UK:Academia Press—Elsevier, vol. 9:401-424 (Jan. 1, 2008).
Sarup et al., "Characterization of an anti-P185\\\superscript:HER2\\\ monoclonal antibody that stimulates receptor function and Inhibits tumor cell growth" Growth Regulat 1:72-82 ( 1991).
Schaefer et al., "γ-Heregulin: A novel heregulin isoform that is an autocrine growth factor for the human breast cancer cell line, MDA-MB-175" Oncogene 15:1385-1394 ( 1997).
Schauenstein, E., et al., "Reactive Disulfide Bonds in Immunoglobuling" Biochem Mol Biol Int 40(3):433-446 (Oct. 1, 1996).
Scott et al., "p185\\\superscript:HER2\\\ signal transduction in breast cancer cells" J Biol Chem 266(22):14300-14305 (Aug. 5, 1991).
Sears, D.W., et al., "Relative Susceptibilities of the Interchain Disulfides of an" Biochemistry—US 16(9):2031-2035 (Jan. 1, 1977).
Shawver, L. K. et al., "Ligand-Like Effects Induced by Anti-c-erbB-2 Antibodies Do Not Correlate with and Are Not Required for Growth Inhibition of Human Carcinoma Cells" Cancer Res 54(5):1367-1373 (Mar. 1, 1994).

(56) References Cited

OTHER PUBLICATIONS

Shepard et al., "Monoclonal antibody therapy of human cancer: Taking the HER2 protooncogene to the clinic" J Clin Immunol 11(3):117-127 ( 1991).
Sigma-Aldrich, Buffet Chart, Useful pH Ranges of Selected Biological Buffers., pp. 1-2 (2000).
Slamon et al., "Human breast cancer: Correlation of relapse and survival with amplification of the HER-2/neu oncogene" Science 235:177-182 (Jan. 9, 1987).
Slamon et al., "Studies of the HER-2/neu proto-oncogene in human breast and ovarian cancer" Science 244:707-712 (May 12, 1989).
Sliwkowski et al., "Coexpression of erbB2 and erbB3 Proteins Reconstitutes a High Affinity Receptor for Heregulin" J Biol Chem 269(20):14661-14665 (May 20, 1994).
Stancovski et al. et al., "Mechanistic Aspects of the Opposing Effects of Monoclonal Antibodies to the ERBB2 Receptor on Tumor Growth" P Natl Acad Sci USA 88(19):8691-8695 (Oct. 1, 1991).
Tagliabue, E. et al., "Selection of Monoclonal Antibodies Which Induce Internalization and Phosphorylation of p185\\\superscript:HER2\\\ and Growth Inhibition of Cells With HER2/NEU Gene Amplification" Int J Cancer 47(6):933-937 (Apr. 1, 1991).
Taylor, F.R., et al., "Suppression of sodium dodecyl sulfate-polyacrylamide gel" Anal Biochem 353:204-208 (Mar. 9, 2006).
Thakur, M., et al., "Determination of Reduced Disulfide Groups in Monoclonal Antibodies" Biotechniques 8(5):512-516 (May 1, 1990).
Thermo Scientific, Product Manual for ProPac WCX-10 and ProPac SCX-10, Document No. 031410-08, Oct. 1, 2015, pp. 1-28.
Tous et al., "Characterization of a novel modification to monoclonal antibodies: thioether cross-link of heavy and light chains" Anal. Chem. 77:2675-2682 ( 2005).
Trexler-Schmidt et al., "Identification and Prevention of Antibody Disulfide Bond Reduction During Cell Culture Manufacturing" Biotechnology and Bioengineering 106(3):452-461 (Jun. 15, 2010).
Virella, G., et al., "Sensitivity to Reduction of Human Immunoglobuling of Different Heavy Chain Subclasses" Immunnochemistry 10:213-217 (Apr. 5, 1972).
Vitetta and Uhr, "Monoclonal antibodies as agonists: An expanded role for their use in cancer therapy" Cancer Res 54(20):5301-5309 (Oct. 15, 1994).
Vlasak et al., "Heterogeneity of monoclonal Antibodies Revealed by charge-Sensitive Methods" Current Pharmaceutical Biotechnology 9:468-481 ( 2008).
Wang et al., "Antibody Structure, Instability, and Formulation" J Pharm Sci 96(1):1-26 (Jan. 2007).
Weinberg, W.C., et al., "Development and regulation of monoclonal antibody products: Challenges" Cancer Metast Rev 24:569-584 (Jan. 1, 2005).
Weiner et al., "Expression of the neu Gene-encoded Protein (P185\\\superscript:neu\\\) in Human Non-Small Cell Carcinomas of the Lung" Cancer Res 50(2):421-425 (Jan. 15, 1990).
Williams et al., "Expression of c-erbB-2 in Human Pancreatic Adenocarcinomas" Pathobiology 59(1):46-52 ( 1991).
Wu et al. et al., "Apoptosis Induced By an Anti-Epidermal Growth Factor Receptor Monoclonal Antibody in a Human Colorectal Carcinoma Cell Line and Its Delay By Insulin" J Clin Invest 95(4):1897-1905 (Apr. 1995).
Wurm, F., "Production of recombinant protein therapeutics in cultivated mammalian cells" Nat. Biotechnol 22(11):1393-1398 (Nov. 4, 2004).
Xu et al., "Antibody-Induced Growth Inhibition is Mediated Through Immunochemically and Functionally Distinct Epitopes on the Extracellular Domain of the c-erbB-2 (HER-2/neu) Gene Product p185" Int J Cancer 53(3):401-408 (Feb. 1, 1993).
Yokota et al., "Amplification of c-erbB-2 Oncogene in Human Adenocarcinomas in Vivo" Lancet 1(8484):765-767 (Apr. 5, 1986).
Yonemura et al., "Evaluation of Immunoreactivity for erbB-2 Protein as a Marker of Poor Short Term Prognosis in Gastric Cancer" Cancer Res 51(3):1034-1038 (Feb. 1, 1991).
Zhang et al., "Free sulfhydryl in recombinant monoclonal antibodies" Biotechnol. Prog. 18:509-513 ( 2002).
Zhang et al., "Neuregulin-3 (NRG3): A novel neural tissue-enriched protein that binds and activates ErbB4" P Natl Acad Sci USA 94:9562-9567 (Sep. 22, 1997).
Zhau et al., "Amplification and Expression of the c-erb B-2/neu Proto-Oncogene in Human Bladder Cancer" Mol Carcinogen 3(5):254-257 ( 1990).
Chowdhury et al., "Origin and Removal of Adducts (Molecular Mass=98 u) Attached to Peptide and Protein Ions in Electrospray Ionization Mass Spectra" American Society for Mass Spectrometry 1(5):372-388 ( 1990).
Declaration of Dr. Andreas Seidl Dated Sep. 3, 2020 With Annex, pp. 1-134.
Declaration of Dr. Markus Blumel Dated Aug. 24, 2020 with Annex, pp. 1-127.
European Medicines Agency Comparability of Biotechnological/Biological Products Jun. 2005, pp. 1-13.
European Medicines Agency Test Procedures and Acceptance Criteria for Biotechnological Products Sep. 1999, pp. 1-17.
Harris et al., "Commercial Manufacturing Scale Formulation and Analytical Characterization of Therapeutic Recombinant Antibodies" Drug Development Research 61:137-154 ( 2004).
Motchnik et al., "Acidic Variants of Monoclonal Antibodies: Origins, Characteristics and Impact on Pharmacokinetics" Abstract (2008).
Ozturk, S. S.,CRC Press, Taylor & Francis Group, ( 2006).
Quan et al., "A Study in Glycation of a Therapeutic Recombinant Humanized Monoclonal Antibody: Where it is, how it got there, and how it affects charge-based Behavior" Anal Biochem 237:179-191 ( 2008).
Sigma-Aldrich, "Glucose in Cell Culture, Importance and Uses of Glucose in Serum-Free Eucaryotic, including Hybridoma and Chinese Hamster Ovary (CHO) Cell, Cultures" ( Aug. 27, 2006).

Variable Light

```
              10          20              30          40
2C4    DTVMTQSHKIMSTSVGDRVSITC  [KASQDVSIGVA]  WYQQRP
       **    ****  *           *                    *
574    DIQMTQSPSSLSASVGDRVTITC  [KASQDVSIGVA]  WYQQKP
                                  *   **  ***
hum κI DIQMTQSPSSLSASVGDRVTITC  [RASQSISNYLA]  WYQQKP 50          60              70          80
2C4    GQSPKLLIY  [SASYRYT]  GVPDRFTGSGSTDFTFTISSVQA
       **                        *  *           *   * *
574    GKAPKLLIY  [SASYRYT]  GVPSRFSGSGSGTDFTLTISSLQP
                   * *****
hum κI GKAPKLLIY  [AASSLES]  GVPSRFSGSGSGTDFTLTISSLQP 90         100
2C4    EDLAVYYC  [QQYYIYPYT]  FGGGTKLEIK  (SEQ ID NO:1)
         * *                    *    *
574    EDFATYYC  [QQYYIYPYT]  FGQGTKVEIK  (SEQ ID NO:3)
                   *** *
hum κI EDFATYYC  [QQYNSLPWT]  FGQGTKVEIK  (SEQ ID NO:5)
```

*FIG. 2A*

Variable Heavy

```
               10           20             30           40
2C4     EVQLQQSGPELVKPGTSVKISCKAS  [GFTFTDYTMD]  WVKQS
          **    **   *   * *** *                       * *
574     EVQLVESGGGLVQPGGSLRLSCAAS  [GFTFTDYTMD]  WVRQA
                                      ** * *
hum III EVQLVESGGGLVQPGGSLRLSCAAS  [GFTFSSYAMS]  WVRQA 50    a     60              70            80
2C4     HGKSLEWIG  [DVNPNSGGSIYNQRFKG]  KASLTVDRSSRIVYM
        *  *  **                        *** *    **** *
574     PGKGLEWVA  [DVNPNSGGSIYNQRFKG]  RFTLSVDRSKNTLYL
                    ****** *** ****        *  *
hum III PGKGLEWVA  [VISGDGGSTYYADSVKG]  RFTISRDNSKNTLYL abc        90       100ab           110
2C4     ELRSLTFEDTAVYYCAR  [NLGPSFYFDY]  WGQGTTLTVSS  (SEQ ID NO:2)
        *** **                                 * *
574     QMNSLRAEDTAVYYCAR  [NLGPSFYFDY]  WGQGTLVTVSS  (SEQ ID NO:4)
                              ********
hum III QMNSLRAEDTAVYYCAR  [GRVGYSLYDY]  WGQGTLVTVSS  (SEQ ID NO:6)
```

*FIG. 2B*

Amino Acid Sequence for Pertuzumab Light Chain

```
  1         10        20        30        40        50        60
  |         |         |         |         |         |         |
DIQMTQSPSSLSASVGDRVTITCKASQDVSIGVAWYQQKPGKAPKLLIYSASYRYTGVPS 70        80        90       100       110       120
            |         |         |         |         |         |
RFSGSGSGTDFTLTISSLQPEDFATYYCQQYYIYPYTFGQGTKVEIKRTVAAPSVFIFPP 130       140       150       160       170       180
            |         |         |         |         |         |
SDEQLKSGTASVVCLLNNFYPREAKVQWKVDNALQSGNSQESVTEQDSKDSTYSLSSTLT 190       200       210
            |         |         |
LSKADYEKHKVYACEVTHQGLSSPVTKSFNRGEC
```

*FIG. 3A*

Amino Acid Sequence for Pertuzumab Heavy Chain

```
  1         10        20        30        40        50        60
  |         |         |         |         |         |         |
EVQLVESGGGLVQPGGSLRLSCAASGFTFTDYTMDWVRQAPGKGLEWVADVNPNSGGSIY 70        80        90       100       110       120
            |         |         |         |         |         |
NQRFKGRFTLSVDRSKNTLYLQMNSLRAEDTAVYYCARNLGPSFYFDYWGQGTLVTVSSA 130       140       150       160       170       180
            |         |         |         |         |         |
STKGPSVFPLAPSSKSTSGGTAALGCLVKDYFPEPVTVSWNSGALTSGVHTFPAVLQSSG 190       200       210       220       230       240
            |         |         |         |         |         |
LYSLSSVVTVPSSSLGTQTYICNVNHKPSNTKVDKKVEPKSCDKTHTCPPCPAPELLGGP 250       260       270       280       290       300
            |         |         |         |         |        *|
SVFLFPPKPKDTLMISRTPEVTCVVVDVSHEDPEVKFNWYVDGVEVHNAKTKPREEQYNS 310       320       330       340       350       360
            |         |         |         |         |         |
TYRVVSVLTVLHQDWLNGKEYKCKVSNKALPAPIEKTISKAKGQPREPQVYTLPPSREEM 370       380       390       400       410       420
            |         |         |         |         |         |
TKNQVSLTCLVKGFYPSDIAVEWESNGQPENNYKTTPPVLDSDGSFFLYSKLTVDKSRWQ 430       440       448
            |         |         |
QGNVFSCSVMHEALHNHYTQKSLSLSPG
```

*FIG. 3B*

```
1                             15                            30                            45
MGWSCIIFFLVATATGVHSDIQMTQSPSSLSASVGDRVTITCKAS 46                            60                            75                            90
QDVSIGVAWYQQKPGKAPKLLIYSASYRYTGVPSRFSGSGSGTDF 91                            105                           120                           135
TLTISSLQPEDFATYYCQQYYIYPYTFGQGTKVEIKRTVAAPSVF 136                           150                           165                           180
IFPPSDEQLKSGTASVVCLLNNFYPREAKVQWKVDNALQSGNSQE 181                           195                           210                           225
SVTEQDSKDSTYSLSSTLTLSKADYEKHKVYACEVTHQGLSSPVT 226      233
KSFNRGEC              (SEQ ID NO. 17)
```

```
  1 MGWSCIIFFL VATATGVHSE VQLVESGGGL VQPGGSLRLS CAASG
 46 FTFTDYTMDW VRQAPGKGLE WVADVNPNSG GSIYNQRFKG RFTLS
 91 VDRSKNTLYL QMNSLRAEDT AVYYCARNLG PSFFYFDYWG QGTLVT
136 VSSASTKGPS VFPLAPSSKS TSGGTAALGC LVKDYFPEPV TVSWN
181 SGALTSGVHT FPAVLQSSGL YSLSSVVTVP SSSLGTQTYI CNVNH
226 KPSNTKVDKK VEPKSCDKTH TCPPCPAPEL LGGPSVFLFP PKPKD
271 TLMISRTPEV TCVVVDVSHE DPEVKFNWYV DGVEVHNAKT KPREE
316 QYNSTYRVVS VLTVLHQDWL NGKEYKCKVS NKALPAPIEK TISKA
361 KGQPREPQVY TLPPSREEMT KNQVSLTCLV KGFYPSDIAV EWESN
406 GQPENNYKTT PPVLDSDGSF FLYSKLTVDK SRWQQGNVFS CSVMH
451 EALHNHYTQK SLSLSPG (SEQ ID NO. 18)
```

Light Chain

```
1                          15                          30                          45
DIQMTQSPSSLSASVGDRVTITCRASQDVNTAVAWYQQKPGKAPK 46                         60                          75                          90
LLIYSASFLYSGVPSRFSGSRSGTDFTLTISSLQPEDFATYYCQQ 91                         105                         120                         135
HYTTPPTFGQGTKVEIKRTVAAPSVFIFPPSDEQLKSGTASVVCL 136                        150                         165                         180
LNNFYPREAKVQWKVDNALQSGNSQESVTEQDSKDSTYSLSSTLT 181                        195                         210    214
LSKADYEKHKVYACEVTHQGLSSPVTKSFNRGEC
```

FIG. 8A

Heavy Chain

```
1   VHSDIQMTQSPSSLSASVGDRVTITCKASQDVSIGVAWYQQKPGK  45
46  APKLLIYSASYRYTGVPSRFSGSGSGTDFTLTISSLQPEDFATYY  90
91  CQQYYIYPYTFGQGTKVEIKRTVAAPSVFIFPPSDEQLKSGTASV  135
136 VCLLNNFYPREAKVQWKVDNALQSGNSQESVTEQDSKDSTYSLSS  180
181 TLTLSKADYEKHKVYACEVTHQGLSSPVTKSFNRGEC          217  (SEQ ID NO. 23)
```

```
  1  EVQLVESGGG LVQPGGSLRL SCAASGFFTD YTMDWVRQAP GKGL
 46  EWVADVNPNS GGSIYNQRFK GRFTLSVDRS KNTLYLQMNS LRAED
 91  TAVYYCARNL GPSVKDYFFD YWGQGTLVTV SSGPSVFPLA PSSK
136  STSGGTAALG CLVKDYFPEP VTVSWNSGAL TSGVHTFPAV LQSSG
181  LYSLSSVVTV PSSSLGTQTY ICNVNHKPSN TKVDKKVEPK SCDKT
226  HTCPPCPAPE LLGGPSVFLF PPKPKDTLMI SRTPEVTCVV VDVSH
271  EDPEVKFNWY VDGVEVHNAK TKPREEQYNS TYRVVSVLTV LHQDW
316  LNGKEYKCKV SNKALPAPIE KTISKAKGQP REPQVYTLPP SREEM
361  TKNQVSLTCL VKGFYPSDIA VEWESNGQPE NNYKTTPPVL DSDGS
406  FFLYSKLTVD KSRWQQGNVF SCSVMHEALH NHYTQKSLSL SPGK
                                                  449
```

(SEQ ID NO. 24)

| Analysis of Pertuzumab Starting Material and CEX Fractions | | | |
|---|---|---|---|
| Analysis | Starting Material | Main Peak | Acidic Variants |
| CEX (%AV, %MP, %BV) | 21, 68, 12 | 5, 93, 2 | 95, 4, 2 |
| Potency | 94 (Ave. n=2) | 109 | 92 |
| SEC (% Monomer) | 99.9 | 99.9 | 100 |

| Main Peak Incubation Conditions ||
|---|---|
| 12d Incubation Sample Condition | % CEX Main Peak |
| Time Zero | 90-92 |
| Fresh Media | 41% |
| Spent Media | 49% |
| -Glucose | 43% |
| -Glucose, -Peptone, -Pluronic | 41% |
| Fresh Media + ProA Isolation | 37% |
| Media Buffer | 56% |

*FIG. 14*

| Methods for Characterization of Acidic Variants ||
|---|---|
| Method | Variants Detected* |
| CEX +/- Sialidase Treatment | 6% Sialylated |
| Reduced CE-SDS | 1.5% Incompletely Reduced |
| Non-reduced CE-SDS | 6% Reduced Disulfide |
| Boronate Chromatography | 3.5% Glycated (Higher Order) |
| Peptide Map | Deamidated |

* Percent of Total CEX Peak Area.

*FIG. 15*

| AUC and Geometric Mean Ratios from PK Study | | | |
|---|---|---|---|
| Test Material (n=12 for Each Group) | $AUC_{0-14}$ (Day · µg/mL) | | Geometric Mean Ratio (CI) |
| | Mean ± SD | Geometric Mean | |
| Acidic Variant | 910 ± 73.1 | 907 | 0.963 (0.905, 1.03) |
| Main Peak | 895 ± 85.5 | 891 | 0.946 (0.884, 1.01) |
| Pertuzumab Starting Material | 946 ± 94.6 | 942 | NA |

COMPOSITION COMPRISING ANTIBODY THAT BINDS TO DOMAIN II OF HER2 AND ACIDIC VARIANTS THEREOF

CROSS-REFERENCE TO RELATED APPLICATIONS

This application is a divisional application of U.S. application Ser. No. 15/450,509, filed on Mar. 6, 2017, which is a continuation application of U.S. application Ser. No. 14/162,255, filed Jan. 23, 2014, which is a divisional application of U.S. application Ser. No. 12/361,180, filed on Jan. 28, 2009, now U.S. Pat. No. 8,652,474 which claims priority under 35 USC § 119(e) to U.S. Provisional Application No. 61/024,825, filed on Jan. 30, 2008, the disclosures of which are hereby incorporated by reference in entirety for all purposes

FIELD OF THE INVENTION

The present invention concerns a composition comprising a main species HER2 antibody that binds to domain II of HER2, and acidic variants thereof. The invention also relates to pharmaceutical formulations comprising the composition, and therapeutic uses for the composition.

BACKGROUND OF THE INVENTION

HER2 Antibodies

The HER family of receptor tyrosine kinases are important mediators of cell growth, differentiation and survival. The receptor family includes four distinct members including epidermal growth factor receptor (EGFR, ErbB1, or HER1), HER2 (ErbB2 or $p185^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn, supra; Masui et al. *Cancer Research* 44:1002-1007 (1984); and Wu et al. *J. Clin. Invest.* 95:1897-1905 (1995).

The second member of the HER family, $p185^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet:* 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al. *Br. J. Cancer* 57:358-363 (1988); Williams et al. *Pathobiology* 59:46-52 (1991); and McCann et al., *Cancer*, 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat $p185^{neu}$ and human HER2 protein products have been described. Drebin and colleagues have raised antibodies against the rat neu gene product, $p185^{neu}$. See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of $p185^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2): 979-986 (1991); Lewis et al. *Cancer Immunol. Immunother.* 37: 255-263 (1993); Pietras et al. *Oncogene* 9: 1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, Trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS* (USA) 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appin No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS* (USA) 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

To target the HER signaling pathway, rhuMAb 2C4 (Pertuzumab) was developed as a humanized antibody that inhibits the dimerization of HER2 with other HER receptors, thereby inhibiting ligand-driven phosphorylation and activation, and downstream activation of the RAS and AKT pathways. In a phase I trial of Pertuzumab as a single agent for treating solid tumors, 3 subjects with advanced ovarian cancer were treated with pertuzumab. One had a durable partial response, and an additional subject had stable disease for 15 weeks. Agus et al. *Proc Am Soc Clin Oncol* 22: 192, Abstract 771 (2003).

Antibody Variant Compositions

U.S. Pat. No. 6,339,142 describes a HER2 antibody composition comprising a mixture of anti-HER2 antibody and one or more acidic variants thereof, wherein the amount of the acidic variant(s) is less than about 25%. Trastuzumab is the exemplified HER2 antibody.

Reid et al. Poster presented at Well Characterized Biotech Pharmaceuticals conference (January, 2003) "Effects of Cell Culture Process Changes on Humanized Antibody Characteristics" describes an unnamed, humanized IgGlantibody composition with N-terminal heterogeneities due to combinations of VHS signal peptide, N-terminal glutamine, and pyroglutamic acid on the heavy chain thereof.

Harris et al. "The Ideal Chromatographic Antibody Characterization Method" talk presented at the IBC Antibody Production Conference (February, 2002) reports a VHS extension on the heavy chain of E25, a humanized anti-IgE antibody.

Rouse et al. Poster presented at WCBP 'Top Down' Glycoprotein Characterization by High Resolution Mass Spectrometry and Its Application to Biopharmaceutical Development" (Jan. 6-9, 2004) describes a monoclonal antibody composition with N-terminal heterogeneity resulting from $^{-3}$AHS or $^{-2}$HS signal peptide residues on the light chain thereof.

In a presentation at IBC Meeting (September, 2000) "Strategic Use of Comparability Studies and Assays for Well Characterized Biologicals," Jill Porter discussed a late-eluting form of ZENAPAX® with three extra amino acid residues on the heavy chain thereof.

US2006/0018899 describes a composition comprising a main species pertuzumab antibody and an amino-terminal leader extension variant, as well as other variant forms of the pertuzumab antibody.

SUMMARY OF THE INVENTION

According to a first aspect, the invention concerns a composition comprising a main species HER2 antibody that binds to domain II of HER2, and acidic variants thereof wherein the acidic variants include glycated variant, disulfide reduced variant, or non-reducible variant. Preferably, the acidic variants include glycated variant, deamidated variant, disulfide reduced variant, sialylated variant, and non-reducible variant. Desirably, the amount of the acidic variants is less than about 25%.

In another aspect, the invention provides a composition comprising a main species HER2 antibody comprising variable light and variable heavy sequences in SEQ ID Nos. 3 and 4, respectively, and acidic variants of the main species antibody, wherein the acidic variants include glycated variant, deamidated variant, disulfide reduced variant, sialylated variant, and non-reducible variant.

The invention also concerns pharmaceutical formulations comprising the compositions in a pharmaceutically acceptable carrier.

Additionally, the invention relates to a method of treating HER2 positive cancer in a patient comprising administering the pharmaceutical formulation to the patient in an amount effective to treat the cancer. With respect to such methods, as demonstrated in the Example herein, preferably the main species antibody and acidic variants have essentially the same pharmacokinetics.

In another aspect, the invention concerns a method of making a pharmaceutical composition comprising: (1) preparing a composition comprising a main species HER2 antibody that binds to domain II of HER2, and acidic variants thereof including glycated variant, disulfide reduced variant, or non-reducible variant, and (2) evaluating the acidic variants in the composition, and confirming that the amount thereof is less than about 25%. In one embodiment, the acidic variants are evaluated by a method selected from the group consisting of ion exchange chromatography wherein the composition is treated with sialidase, reduced capilliary electrophoresis with sodium dodecyl sulfate (CE-SDS), non-reduced CE-SDS, boronate chromatography, and peptide mapping.

BRIEF DESCRIPTION OF THE DRAWINGS

FIGS. 2A and 2B depict alignments of the amino acid sequences of the variable light ($V_L$) (FIG. 2A) and variable heavy (VII) (FIG. 2B) domains of murine monoclonal antibody 2C4 (SEQ ID Nos. 1 and 2, respectively); $V_L$ and $V_H$ domains of humanized 2C4 version 574 (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

FIGS. 3A and 3B show the amino acid sequences of Pertuzumab light chain (SEQ ID No. 15) and heavy chain (SEQ ID No. 16). CDRs are shown in bold. The carbohydrate moiety is attached to Asn 299 of the heavy chain.

FIGS. 4A and 4B show the amino acid sequences of Pertuzumab light chain (SEQ ID No. 17) and heavy chain (SEQ ID No. 18), each including an intact amino terminal signal peptide sequence.

FIGS. 8A and 8B show the amino acid sequences of Trastuzumab light chain (SEQ ID No. 13) and heavy chain (SEQ ID No. 14).

FIGS. 9A and 9B depict a variant Pertuzumab light chain sequence (SEQ ID No. 23) and a variant Pertuzumab heavy chain sequence (SEQ ID No. 24).

FIG. 14 describes main peak incubation conditions.

FIG. 15 summarizes methods for characterization of acidic variants.

DETAILED DESCRIPTION OF THE PREFERRED EMBODIMENTS

I. Definitions

Figure 1:
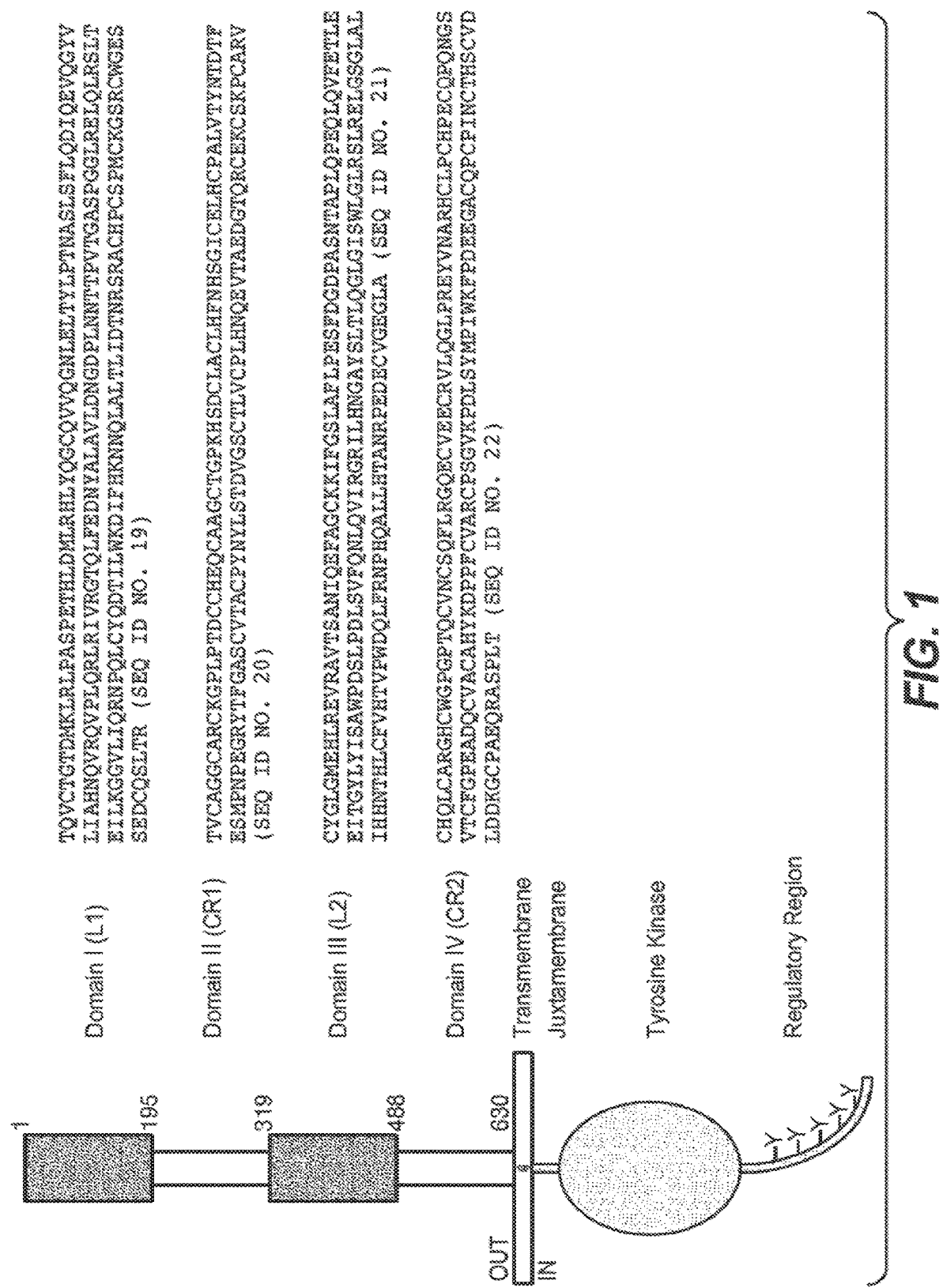
FIG. 1 provides a schematic of the HER2 protein structure, and amino acid sequences for Domains I-IV (SEQ ID Nos.19-22, respectively) of the extracellular domain thereof.
Figure 5:
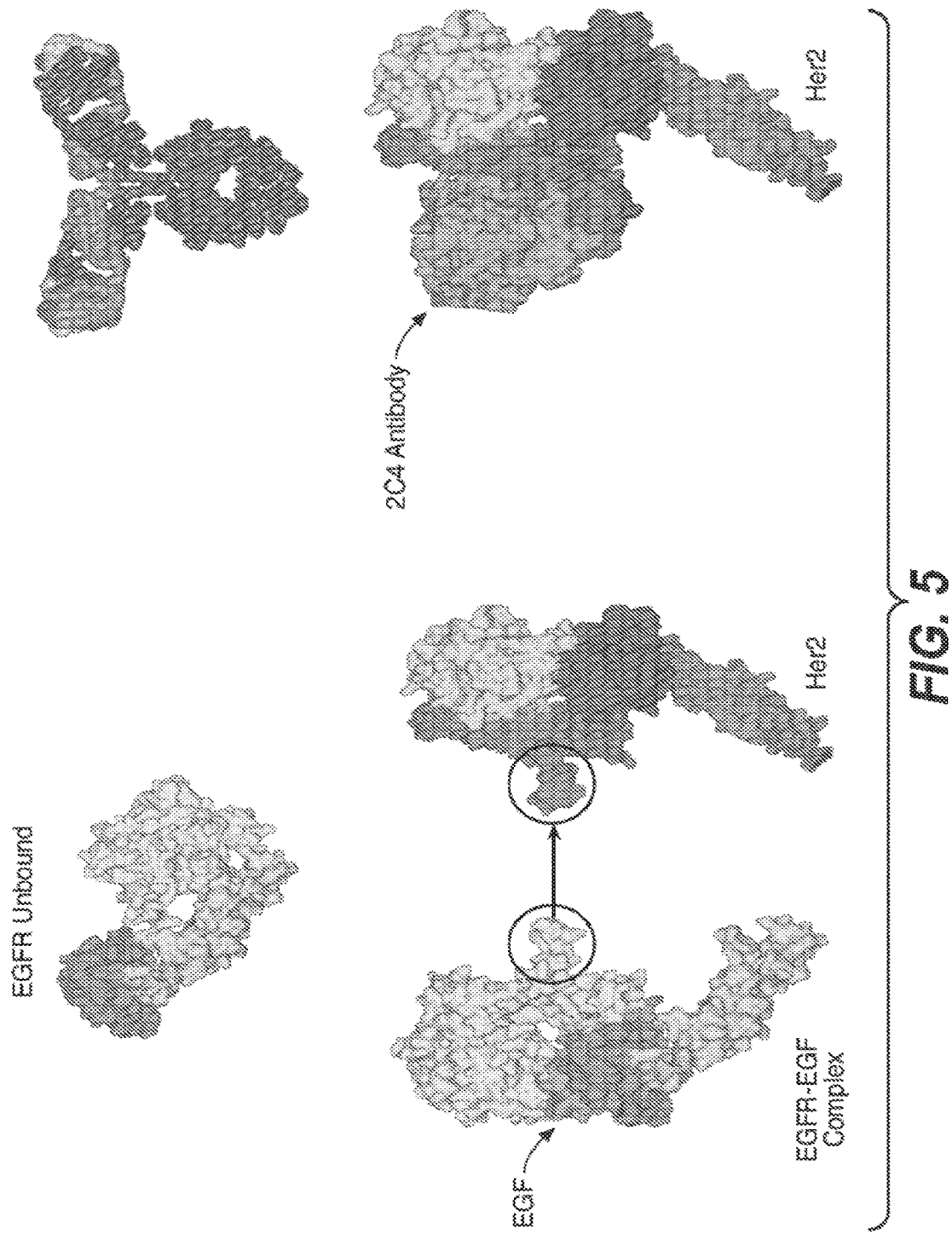
FIG. 5 depicts, schematically, binding of 2C4 at the heterodimeric binding site of HER2, thereby preventing heterodimerization with activated EGFR or HER3.
Figure 6:
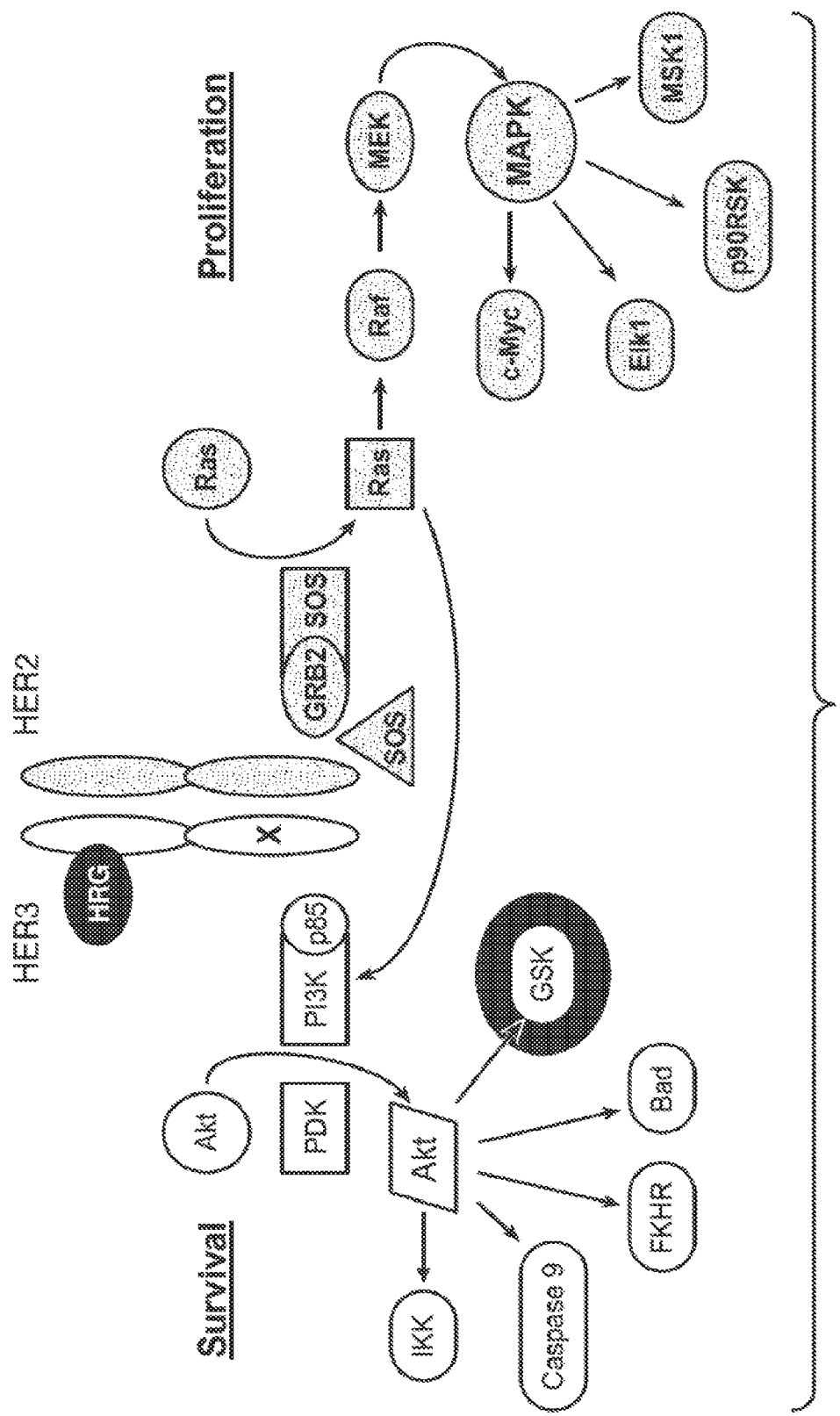
FIG. 6 depicts coupling of HER2/HER3 to the MAPK and Akt pathways.
Figure 7:
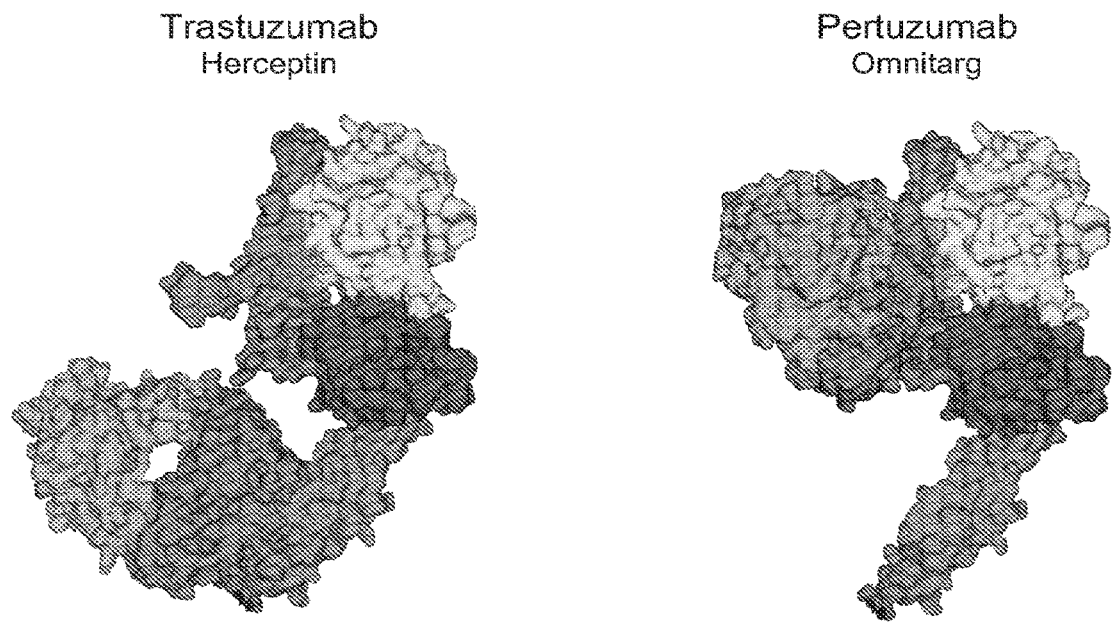
FIG. 7 compares activities of Trastuzumab and Pertuzumab.

The term "main species antibody" herein refers to the antibody amino acid sequence structure in a composition which is the quantitatively predominant antibody molecule in the composition. Preferably, the main species antibody is a HER2 antibody, such as an antibody that binds to Domain II of HER2, antibody that inhibits HER dimerization more effectively than Trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, and more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. a deamidated antibody variant), a basic variant, the antibody with an amino-terminal leader extension (e.g. VHS-) on one or two light chains thereof, antibody with a C-terminal lysine residue on one or two heavy chains thereof, antibody with one or more oxidized methionine residues, etc. and includes combinations of variations to the amino acid sequences of heavy and/or light chains.

An "acidic variant" is a variant of the main species antibody which is more acidic than the main species antibody. An acidic variant has gained negative charge or lost positive charge relative to the main species antibody. Such acidic variants can be resolved using a separation methodology, such as ion exchange chromatography, that separates proteins according to charge. Acidic variants of a main species antibody elute earlier than the main peak upon separation by cation exchange chromatography.

A "disulfide reduced variant" has one more disulfide-bonded cysteine(s) chemically reduced to the free thiol form. This variant can be monitored by hydrophobic interaction chromatography or by sizing methodology such as Capillary Electrophoresis with Sodium Dodecyl Sulfate (CE-SDS), e.g. as described in Example 1. Herein, a "non-reducible variant" is a variant of the main species antibody that cannot be chemically reduced to heavy and light chain by treatment with a reducing agent such as dithiothreitol. Such variants can be assessed by treating the composition with a reducing agent and evaluating the resulting composition using a methodology that evaluates protein size, such as Capillary Electrophoresis with Sodium Dodecyl Sulfate (CE-SDS), for instance using the techniques described in Example 1 below.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, antibody which is syalidated, etc, as well as combinations of such glycosylation alterations.

Where the antibody has an Fc region, an oligosaccharide structure such as that shown in FIG. 14 herein may be attached to one or two heavy chains of the antibody, e.g. at residue 299. For Pertuzumab, G0 was the predominant oligosaccharide structure, with other oligosaccharide structures such as G0-F, G-1, Man5, Man6, G1-1, G1(1-6), G1(1-3) and G2 being found in lesser amounts in the Pertuzumab composition.

Unless indicated otherwise, a "G1 oligosaccharide structure" herein includes G1(1-6) and G1(1-3) structures.

For the purposes herein, "sialylated variant" is a variant of the main species antibody comprising one or more sialylated carbohydrate moieties attached to one or two heavy chains thereof. A sialylated variant can be identified by evaluating a composition (for example by ion exchange chromatography) with or without sialidase treatment, e.g. as described in the example.

A "glycated variant" is an antibody to which a sugar, such as glucose, has been covalently attached. This addition can occur by reaction of glucose with a lysine residue on the protein (e.g. in cell culture media). A glycated variant can be identified by mass spectrometry analysis of the reduced antibody evaluating the increase in mass of heavy or light chains. A glycated variant can also be quantified by boronate chromatography as explained in Example 1 below. A glycated variant differs from a glycosylation variant.

A "deamidated" antibody is one in which one or more asparagine residues thereof has been derivitized, e.g. to an aspartic acid, a succinimide, or an iso-aspartic acid. An example of a deamidated antibody is a pertuzumab variant, wherein Asn-386 and/or Asn-391 on one or two heavy chains of pertuzumab are deamidated.

A "amino-terminal leader extension variant" herein refers to a main species antibody with one or more amino acid residues of the amino-terminal leader sequence at the amino-terminus of any one or more heavy or light chains of the main species antibody. An exemplary amino-terminal leader extension comprises or consists of three amino acid residues, VHS, present on one or both light chains of an antibody variant.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

For the purposes herein, "cation exchange analysis" refers to any method by which a composition comprising two or more compounds is separated based on charge differences using a cation exchanger. A cation exchanger generally comprises covalently bound, negatively charged groups. Preferably, the cation exchanger herein is a weak cation-exchanger and/or comprises a carboxylate functional group, such as the PROPAC WCX-10® cation exchange column sold by Dionex.

A "HER receptor" is a receptor protein tyrosine kinase which belongs to the HER receptor family and includes EGFR, HER2, HER3 and HER4 receptors and other members of this family to be identified in the future. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. Preferably the HER receptor is native sequence human HER receptor.

The extracellular domain of HER2 comprises four domains, Domain I (amino acid residues from about 1-195), Domain II (amino acid residues from about 196-319), Domain III (amino acid residues from about 320-488), and Domain IV (amino acid residues from about 489-630) (residue numbering without signal peptide). See Garrett et al. *Mol. Cell.* 11: 495-505 (2003), Cho et al. Nature 421: 756-760 (2003), Franklin et al. *Cancer Cell* 5:317-328 (2004), or Plowman et al. *Proc. Natl. Acad. Sci.* 90:1746-1750 (1993). See, also, FIG. 1 herein.

The terms "ErbB1", "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appin. No 599,274; Plowman et al., *Proc. Natl. Acad. Sci. USA*, 90:1746-1750 (1993); and Plowman et al., *Nature*, 366:473-475 (1993), including isoforms thereof, e.g., as disclosed in WO99/19488, published Apr. 22, 1999.

By "HER ligand" is meant a polypeptide which binds to and/or activates an HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260

(1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362:312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1$_{177\text{-}244}$).

A "HER dimer" herein is a noncovalently associated dimer comprising at least two different HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20):14661-14665 (1994), for example. Examples of such HER dimers include EGFR-HER2, HER2-HER3 and HER3-HER4 heterodimers. Moreover, the HER dimer may comprise two or more HER2 receptors combined with a different HER receptor, such as HER3, HER4 or EGFR. Other proteins, such as a cytokine receptor subunit (e.g. gp130) may be associated with the dimer.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such as those variants described herein. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact antibody" is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variants thereof. Preferably, the intact antibody has one or more effector functions, and comprises an oligosaccharide structure attached to one or two heavy chains thereof.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise herein, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991). The "EU index as in Kabat" refers to the residue numbering of the human IgG1 EU antibody.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9: 457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of*

*Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, Rosenburg and Moore eds., Springer-Verlag, N.Y., pp. 269-315 (1994). HER2 antibody scFv fragments are described in WO93/16185; U.S. Pat. Nos. 5,571,894; and 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337, expressly incorporated herein by reference; humanized 520C9 (WO93/21319) and humanized 2C4 antibodies as described herein.

For the purposes herein, "Trastuzumab," "HERCEPTIN®," and "huMAb4D5-8" refer to an antibody comprising the light and heavy chain amino acid sequences in SEQ ID NOS. 13 and 14, respectively.

Herein, "Pertuzumab" and "rhuMAb 2C4," refer to an antibody comprising the variable light and variable heavy amino acid sequences in SEQ ID Nos. 3 and 4, respectfully. Where Pertuzumab is an intact antibody, it preferably comprises the light chain and heavy chain amino acid sequences in SEQ ID Nos. 15 and 16, respectively.

A "naked antibody" is an antibody (as herein defined) that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A HER2 antibody which "inhibits HER dimerization more effectively than Trastuzumab" is one which reduces or eliminates HER dimers more effectively (for example at least about 2-fold more effectively) than Trastuzumab. Preferably, such an antibody inhibits HER2 dimerization at least about as effectively as an antibody selected from the group consisting of intact murine monoclonal antibody 2C4, a Fab fragment of murine monoclonal antibody 2C4, intact Pertuzumab, and a Fab fragment of Pertuzumab. One can evaluate HER dimerization inhibition by studying HER dimers directly, or by evaluating HER activation, or downstream signaling, which results from HER dimerization, and/or by evaluating the antibody-HER2 binding site, etc. Assays for screening for antibodies with the ability to inhibit HER dimerization more effectively than Trastuzumab are described in Agus et al. *Cancer Cell* 2: 127-137 (2002) and WO01/00245 (Adams et al.). By way of example only, one may assay for inhibition of HER dimerization by assessing, for example, inhibition of HER dimer formation (see, e.g., FIG. 1A-B of Agus et al. *Cancer Cell* 2: 127-137 (2002); and WO01/00245); reduction in HER ligand activation of cells which express HER dimers (WO01/00245 and FIG. 2A-B of Agus et al. *Cancer Cell* 2: 127-137 (2002), for example); blocking of HER ligand binding to cells which express HER dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER dimers in the presence (or absence) of HER ligand (WO01/00245 and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

The HER2 antibody may "inhibit HRG-dependent AKT phosphorylation" and/or inhibit "HRG- or TGFα-dependent MAPK phosphorylation" more effectively (for instance at least 2-fold more effectively) than Trastuzumab (see Agus et al. *Cancer Cell* 2: 127-137 (2002) and WO01/00245, by way of example).

The HER2 antibody may be one which does "not inhibit HER2 ectodomain cleavage" (Molina et al. *Cancer Res.* 61:4744-4749(2001)).

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-Pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., Trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2 using methods known in the art and/or one can study the antibody-HER2 structure (Franklin et al. *Cancer Cell* 5:317-328 (2004)) to see what domain(s) of HER2 is/are bound by the antibody. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, in FIG. 1).

The "epitope 7C2/7F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of HER2 in FIG. 1).

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

The term "effective amount" refers to an amount of a drug effective to treat disease in the patient. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response, PR, or complete response, CR), increase overall survival time, and/or improve one or more symptoms of cancer.

A "HER2 positive cancer" is one comprising cells which have HER2 protein present at their cell surface.

A cancer which "overexpresses" a HER receptor is one which has significantly higher levels of a HER receptor, such as HER2, at the cell surface thereof, compared to a noncancerous cell of the same tissue type. Such overexpression may be caused by gene amplification or by increased transcription or translation. HER receptor overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). One may also study HER receptor overexpression by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress HER2 receptor" is one which does not express higher than normal levels of HER2 receptor compared to a noncancerous cell of the same tissue type.

A cancer which "overexpresses" a HER ligand is one which produces significantly higher levels of that ligand compared to a noncancerous cell of the same tissue type. Such overexpression may be caused by gene amplification or by increased transcription or translation. Overexpression of the HER ligand may be determined diagnostically by evaluating levels of the ligand (or nucleic acid encoding it) in the patient, e.g. in a tumor biopsy or by various diagnostic assays such as the IHC, FISH, southern blotting, PCR or in vivo assays described above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK7 polysaccharide complex (JHS Natural Products, Eugene, Oreg.); razoxane; rhizoxin; sizofiran; spirogermanium; tenuazonic acid; triaziquone; 2,2',2®®-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE®), and docetaxel (TAXOTERE®); chlorambucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromedhylornithine (DMFO); retinoids such as retinoic acid, including bexarotene (TARGRETIN®); bisphosphonates such as clodronate (for example, BONEFOS® or OSTAC), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifamib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN®) combined with 5-FU and leucovovin.

Also included in this definition are anti-hormonal agents that act to regulate or inhibit hormone action on tumors such as anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors including vorozole (RIVISOR®), megestrol acetate (MEGASE®), fadrozole, imidazole; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; testolactone; and pharmaceutically acceptable salts, acids or derivatives of any of the above; as well as combinations of two or more of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. I Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib)(IRESSA®) 4-(3=-Chloro-4=fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3 fluorophenyl)methoxy]phenyl] 6[5[[[2methylsulfonyl)ethyl]amino]methyl]-2-furanyl]-4-quinazolinamine; Glaxo-SmithKline) or cyanoguanidine quinazoline and cyanoamidine quinazolamine derivatives.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC_) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines, pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthal-imide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); cyanoguanidine quinazoline and cyanoamidine quinazolamine derivatives; or as described in any of the following patent publications: U.S. Pat. No. 5,804, 396; WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); WO96/33980 (Zeneca); and US2005/0101617.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as Bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

II. HER2 Antibody Variant Compositions

The present invention concerns, at least in part, certain HER2 antibody compositions. Preferably, the HER2 antibody (either or both of the main species HER2 antibody and antibody variant thereof) is one which binds to Domain II of HER2, inhibits HER dimerization more effectively than Trastuzumab, and/or binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

The composition herein comprises a main species HER2 antibody that binds to domain II of HER2, and acidic variants thereof wherein the acidic variants include one, two, or three of glycated variant, disulfide reduced variant, and non-reducible variant. The acidic variants in the composition may include one, two, three, four, or five of glycated variant, deamidated variant, disulfide reduced variant, sialylated variant, and non-reducible variant. Preferably, the total amount of all acidic variants in the composition is less than about 25%. In one embodiment, the glycated variant, deamidated variant, disulfide reduced variant, sialylated variant, and non-reducible variant constitute at least about 75-80% of the acidic variants in the composition.

The invention additionally concerns a composition comprising a main species HER2 antibody comprising variable light and variable heavy sequences in SEQ ID Nos. 3 and 4, respectively, and acidic variants of the main species antibody, wherein the acidic variants include one, two, three, four, or five of glycated variant, deamidated variant, disulfide reduced variant, sialylated variant, and non-reducible variant.

The invention provides a method of making a pharmaceutical composition comprising: (1) preparing a composition comprising a main species HER2 antibody that binds to domain II of HER2, and acidic variants thereof including glycated variant, disulfide reduced variant, or non-reducible variant, and (2) evaluating the acidic variants in the composition, and confirming that the amount thereof is less than about 25%. The method contemplates combining the composition before, during, or after step (2) with a pharmaceutically acceptable carrier. In one embodiment, the composition evaluated in step (2) is in a pharmaceutically acceptable carrier.

In one embodiment, at least about 75-80% of the acidic variants (constituting the less than about 25% of the composition) are selected from: glycated variant, deamidated variant, disulfide reduced variant, sialylated variant, and non-reducible variant.

The acidic variants may be evaluated by a variety of methods, but preferably such methods include one, two, three, four, or five of: ion exchange chromatography (IEC) wherein the composition is treated with sialidase before, after, and/or during the IEC (e.g. to evaluate sialylated variant), reduced CE-SDS (e.g. to evaluate disulfide reduced variant), non-reduced CE-SDS (e.g. to evaluate non-reducible variant), boronate chromatography (e.g. to evaluate glycated variant), and peptide mapping (e.g. to evaluate deamidated variant).

In one embodiment, the overall acidic variants are evaluated by ion exchange chromatography, for example using a weak cation exchanger and/or cation exchanger with carboxylate functional group (for example, using a DIONEX PROPAC WCX-10® chromatography column). In one embodiment of such chromatography the conditions for the chromatography involve Buffer A of 20 mM BisTris, pH 6.0; Buffer B of 20 mM BisTris, 200 mM NaCl, pH 6.0; and a gradient of 0.5% Buffer B at 1.0 mL/min.

The composition optionally includes an amino-terminal leader extension variant. Preferably, the amino-terminal leader extension is on a light chain of the antibody variant (e.g. on one or two light chains of the antibody variant). The main species HER2 antibody or the antibody variant may be an intact antibody or antibody fragment (e.g. Fab of F(ab')$_2$ fragments), but preferably both are intact antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the lower detection limit of any assay (preferably cation exchange analysis) used to detect the variant to an amount less than the amount of the main species antibody. Generally, about 20% or less (e.g. from about 1% to about 15%, for instance from 5% to about 15%, and preferably from about 8% to about 12%) of the antibody molecules in the composition comprise an amino-terminal leader extension. Such percentage amounts are preferably determined using cation exchange analysis.

Further amino acid sequence alterations of the main species antibody and/or variant are contemplated, including but not limited to an antibody comprising a C-terminal lysine residue on one or both heavy chains thereof (such an antibody variant may be present in an amount from about 1% to about 20%), antibody with one or more oxidized methionine residues (for example, Pertuzumab comprising oxidized met-254) etc.

Moreover, aside from the sialylated variant discussed above, the main species antibody or variant may comprise additional glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, etc.

Optionally, the antibody comprising one or two light chains, wherein either or both of the light chains comprise the amino acid sequence in SEQ ID No. 23 (including variants thereof such as those disclosed herein). The antibody further comprises one or two heavy chains, wherein either or both of the heavy chains comprise the amino acid sequence in SEQ ID NO. 16 or SEQ ID NO. 24 (including variants thereof such as those disclosed herein).

The composition may be recovered from a genetically engineered cell line, e.g. a Chinese Hamster Ovary (CHO) cell line expressing the HER2 antibody, or may be prepared by peptide synthesis.

III. Production of HER2 Antibodies

A description follows as to exemplary techniques for the production of the antibodies used in accordance with the present invention. The HER2 antigen to be used for production of antibodies may be, e.g., a soluble form of the extracellular domain of HER2 or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER2 useful for generating antibodies will be apparent to those skilled in the art.

(i) Monoclonal Antibodies

Monoclonal antibodies are obtained from a population of substantially homogeneous antibodies, i.e., the individual antibodies comprising the population are identical and/or bind the same epitope, except for possible variants that may arise during production of the monoclonal antibody, such as those variants described herein. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.,* 130:151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222: 581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(ii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.,* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

U.S. Pat. No. 6,949,245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as intact murine monoclonal antibody 2C4 (or a Fab fragment thereof) and/or binds HER2 essentially as effectively as intact murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest,* 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy complementarity determining residues GFTFTDYTMX, where X is preferably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy amino acid sequence in SEQ ID NO:4.

The humanized antibody may comprise variable light complementarity determining residues KASQDVSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light amino acid sequence in SEQ ID NO:3.

The present application also contemplates affinity matured antibodies which bind HER2 and block ligand activation of a HER receptor. The parent antibody may be a human antibody or a humanized antibody, e.g., one comprising the variable light and/or variable heavy sequences of SEQ ID Nos. 3 and 4, respectively (i.e. variant 574). The affinity matured antibody preferably binds to HER2 receptor with an affinity superior to that of intact murine 2C4 or intact variant 574 (e.g. from about two or about four fold, to about 100 fold or about 1000 fold improved affinity, e.g. as assessed using a HER2-extracellular domain (ECD)

ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

(iii) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(iv) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

(v) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vi) Other Amino Acid Sequence Modifications

Amino acid sequence modification(s) of the HER2 antibodies described herein are contemplated. For example, it may be desirable to improve the binding affinity and/or other biological properties of the antibody. Amino acid sequence variants of the HER2 antibody are prepared by introducing appropriate nucleotide changes into the HER2 antibody nucleic acid, or by peptide synthesis. Such modifications include, for example, deletions from, and/or insertions into and/or substitutions of, residues within the amino acid sequences of the HER2 antibody. Any combination of deletion, insertion, and substitution is made to arrive at the final construct, provided that the final construct possesses the desired characteristics. The amino acid changes also may alter post-translational processes of the HER2 antibody, such as changing the number or position of glycosylation sites.

A useful method for identification of certain residues or regions of the HER2 antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with HER2 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed HER2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a HER2 antibody with an N-terminal methionyl residue or the antibody fused to a cytotoxic polypeptide. Other insertional variants of the HER2 antibody molecule include the fusion to the N- or C-terminus of the HER2 antibody to an enzyme (e.g. for ADEPT) or a polypeptide which increases the serum half-life of the antibody.

Another type of variant is an amino acid substitution variant. These variants have at least one amino acid residue in the HER2 antibody molecule replaced by a different residue. The sites of greatest interest for substitutional mutagenesis include the hypervariable regions or CDRs, but FR or Fc region alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)

2) uncharged polar: Gly (G), Ser (S), Thr (T), Cys (C), Tyr (Y), Asn (N), Gln (Q)

3) acidic: Asp (D), Glu (E)

4) basic: Lys (K), Arg (R), His(H)

Alternatively, naturally occurring residues may be divided into groups based on common side-chain properties:

1) hydrophobic: Norleucine, Met, Ala, Val, Leu, Ile;

(2) neutral hydrophilic: Cys, Ser, Thr, Asn, Gln;

3) acidic: Asp, Glu;

4) basic: His, Lys, Arg;

5) residues that influence chain orientation: Gly, Pro;

6) aromatic: Trp, Tyr, Phe.

Non-conservative substitutions will entail exchanging a member of one of these classes for another class.

Any cysteine residue not involved in maintaining the proper conformation of the HER2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, any oligosaccharide structure attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the oligosaccharide structure attached to an Fc region of the antibody are referenced in WO03/011878, Jean-Mairet et al. and U.S. Pat. No. 6,602,684, Umana et al. Antibodies with at least one galactose residue in an oligosaccharide structure attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof. Antibody compositions comprising main species antibody with such carbohydrate structures attached to one or two heavy chains of the Fc region are contemplated herein.

Nucleic acid molecules encoding amino acid sequence variants of the HER2 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the HER2 antibody.

(vii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the HER2 antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in WO01/00245. HER2 monoclonal antibodies may be added to each well and incubated for 30 minutes. $^{125}$I-labeled rtIRGβ1$_{177}$-224 (25 pm) may then be added, and the incubation may be continued for 4 to 16 hours. Dose response curves may be prepared and an IC$_{50}$ value may be calculated for the antibody of interest. In one embodiment, the antibody which blocks ligand activation of an HER receptor will have an IC$_{50}$ for inhibiting HRG binding to MCF7 cells in this assay of about 50 nM or less, more preferably 10 nM or less. Where the antibody is an antibody fragment such as a Fab fragment, the IC$_{50}$ for inhibiting HRG binding to MCF7 cells in this assay may, for example, be about 100 nM or less, more preferably 50 nM or less.

Alternatively, or additionally, the ability of the HER2 antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in WO01/00245. For example, the MCF7 cells may be plated in 24-well plates and monoclonal antibodies to HER2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at $M_r$–180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an IC$_{50}$ for the antibody of interest may be calculated. In one embodiment, the antibody which blocks ligand activation of a HER receptor will have an IC$_{50}$ for inhibiting HRG stimulation of p180 tyrosine phosphorylation in this assay of about 50 nM or less, more preferably 10 nM or less. Where the antibody is an antibody fragment such as a Fab fragment, the IC$_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g., essentially as described in Schaefer et al. *Oncogene* 15:1385-1394 (1997). According to this assay, MDA-MB-175 cells may be treated with a HER2 monoclonal antibody (10 μg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in WO01/00245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the HER2 antibody is added per dish. After six days, the number of cells, compared to untreated cells are counted using an electronic COULTERJ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FACSCANJ flow cytometer and FACSCONVERTJ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 µg/ml HOECHST 33342® for 2 hr at 37° C., then analyzed on an EPICS ELITE® flow cytometer (Coulter Corporation) using MODFIT LT® software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or Pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(viii) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises a HER2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta^1_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the HER2 antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively, or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. Nos. 6,194,551B1, 6,242,195B1, 6,528,624B1 and 6,538,124 (Idusogie et al.). The antibodies comprise an amino acid substitution at one or more of amino acid positions 270, 322, 326, 327, 329, 313, 333 and/or 334 of the Fc region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et al.).

The HER2 antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

IV. Pharmaceutical Formulations

Therapeutic formulations of the compositions of the present invention are prepared for storage by mixing the composition with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG). Lyophilized HER2 antibody formulations are described in WO 97/04801. Particularly preferred formulations for the present composition are described in US20006/088523.

The formulation herein may also contain more than one active compound as necessary for the particular indication being treated, preferably those with complementary activities that do not adversely affect each other. For example, it may be desirable to further provide antibodies which bind to EGFR, HER2 (e.g. an antibody which binds a different epitope on HER2), HER3, HER4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, EGFR-targeted drug, anti-angiogenic agent, tyrosine kinase inhibitor, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

V. Treatment with the HER2 Antibody Composition

It is contemplated that, according to the present invention, the HER2 antibody may be used to treat cancer. The cancer will generally be HER2 positive, such that the HER2 antibody herein is able to bind to the cancer cells. In one embodiment, the cancer expresses low HER3 (e.g. ovarian cancer) or has elevated HER2:HER3 ratio (e.g. ovarian cancer). Various cancers that can be treated with the composition are listed in the definitions section above.

Preferred cancers to be treated herein include: breast cancer, including HER2 positive breast cancer, optionally in combination with trastuzumab and a taxoid such as docetaxel, and including neoadjuvant therapy of breast cancer; ovarian cancer (including both platinum-resistant and platinum-sensitive ovarian cancer) (see US2006/0013819, for example); lung cancer (including non small cell lung cancer, NSCLC), optionally in combination with an EGFR inhibitor (see US 2007/0020261 for example); colorectal cancer, etc.

It is also contemplated that the HER2 antibody may be used to treat various non-malignant diseases or disorders, such as autoimmune disease (e.g. psoriasis); endometriosis; scleroderma; restenosis; polyps such as colon polyps, nasal polyps or gastrointestinal polyps; fibroadenoma; respiratory disease; cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Preferred non-malignant indications for therapy herein include psoriasis, endometriosis, scleroderma, vascular disease (e.g. restenosis, artherosclerosis, coronary artery disease, or hypertension), colon polyps, fibroadenoma or respiratory disease (e.g. asthma, chronic bronchitis, bronchieactasis or cystic fibrosis).

Treatment with the HER2 antibody will result in an improvement in the signs or symptoms of disease. For instance, where the disease being treated is cancer, such therapy may result in an improvement in survival (overall survival and/or progression free survival) and/or may result in an objective clinical response (partial or complete).

Preferably, the HER2 antibody in the composition administered is a naked antibody. However, the HER2 antibody administered may be conjugated with a cytotoxic agent. Preferably, the immunoconjugate and/or HER2 protein to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The HER2 antibody is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of antibody composition is preferred.

For the prevention or treatment of disease, the appropriate dosage of HER2 antibody will depend on the type of disease to be treated, as defined above, the severity and course of the disease, whether the HER2 antibody is administered for preventive or therapeutic purposes, previous therapy, the patient's clinical history and response to the HER2 antibody, and the discretion of the attending physician. The HER2 antibody is suitably administered to the patient at one time or over a series of treatments. Depending on the type and severity of the disease, about 1 µg/kg to 50 mg/kg (e.g. 0.1-20 mg/kg) of HER2 antibody is an initial candidate dosage for administration to the patient, whether, for example, by one or more separate administrations, or by continuous infusion. In one embodiment, the initial infusion time for the HER2 antibody may be longer than subsequent infusion times, for instance approximately 90 minutes for the initial infusion, and approximately 30 minutes for subsequent infusions (if the initial infusion is well tolerated). The preferred dosage of the HER2 antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the HER2 antibody). An initial higher loading dose, followed by one or more lower doses may be administered. In one embodiment, the HER2 antibody is administered as a loading dose of approximately 840 mg followed by approximately 420 mg administered approximately every 3 weeks. In another embodiment, the HER2 antibody is administered as a loading dose of approximately 1050 mg followed by approximately 525 mg administered approximately every 3 weeks.

Other therapeutic agents may be combined with the HER2 antibody. Such combined administration includes coadministration or concurrent administration, using separate formulations or a single pharmaceutical formulation, and consecutive administration in either order, wherein preferably there is a time period while both (or all) active agents simultaneously exert their biological activities. Thus, the other therapeutic agent may be administered prior to, or following, administration of the HER2 antibody. In this embodiment, the timing between at least one administration of the other therapeutic agent and at least one administration of the HER2 antibody is preferably approximately 1 month or less, and most preferably approximately 2 weeks or less. Alternatively, the other therapeutic agent and the HER2 antibody are administered concurrently to the patient, in a single formulation or separate formulations.

Examples of other therapeutic agents that can be combined with the HER2 antibody include any one or more of: a chemotherapeutic agent, such as an anti-metabolite, e.g. gemcitabine; a second, different HER2 antibody (for example, a growth inhibitory HER2 antibody such as Trastuzumab, or a HER2 antibody which induces apoptosis of a HER2-overexpressing cell, such as 7C2, 7F3 or humanized variants thereof); a second antibody directed against another tumor associated antigen, such as EGFR, HER3, HER4; anti-hormonal compound, e.g., an anti-estrogen compound such as tamoxifen, or an aromatase inhibitor; a cardioprotectant (to prevent or reduce any myocardial dysfunction associated with the therapy); a cytokine; an EGFR-targeted drug (such as Erlitonib, Gefitinib, or Cetuximab); an anti-angiogenic agent (especially Bevacizumab sold by Genentech under the trademark AVASTIN®); a tyrosine kinase inhibitor; a COX inhibitor (for instance a COX-1 or COX-2 inhibitor); non-steroidal anti-inflammatory drug, Celecoxib (CELEBREX®); farnesyl transferase inhibitor (for example, Tipifarnib/ZARNESTRA® R115777 available from Johnson and Johnson or Lonafarnib SCH66336 available from Schering-Plough); antibody that binds oncofetal protein CA 125 such as Oregovomab (MoAb B43.13); HER2 vaccine (such as HER2 AutoVac vaccine from Pharmexia, or APC8024 protein vaccine from Dendreon, or HER2 peptide vaccine from GSK/Corixa); another HER targeting therapy (e.g. trastuzumab, cetuximab, gefitinib, erlotinib, CI1033, GW2016 etc); Raf and/or ras inhibitor (see, for example, WO 2003/86467); Doxil; Topetecan; taxane; GW572016; TLK286; EMD-7200; a medicament that treats nausea such as a serotonin antagonist, steroid, or benzodiazepine; a medicament that prevents or treats skin rash or standard acne therapies, including topical or oral antibiotic; a body temperature-reducing medicament such as acetaminophen, diphenhydramine, or meperidine; hematopoietic growth factor, etc.

Suitable dosages for any of the above coadministered agents are those presently used and may be lowered due to the combined action (synergy) of the agent and HER2 antibody. Treatment with the combination of the HER2 antibody composition and other therapeutic agent may result in a synergistic, or greater than additive, therapeutic benefit to the patient.

If a chemotherapeutic agent is administered, it is usually administered at dosages known therefor, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In addition to the above therapeutic regimes, the patient may be subjected to surgical removal of cancer cells and/or radiation therapy.

VII. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Example. The disclosures of all citations in the specification are expressly incorporated herein by reference.

EXAMPLE 1

This example describes the characterization of a composition comprising a main species HER2 antibody that binds to domain II of HER2 (pertuzumab) and acidic variants thereof.

Pertuzumab is a recombinant humanized monoclonal antibody, generated based on human IgG1(κ) framework. It comprises two heavy chains (448 residues) and two light chains (214 residues). The two heavy chains are linked by two interchain disulfides and each light chain is attached to a heavy chain through one interchain disulfide. There is an N-linked glycosylation site in the Fc region of pertuzumab at Asn-299 of the two heavy chains. Pertuzumab differs from HERCEPTIN® (Trastuzumab) in the epitope binding regions of the light chain (12 amino acid differences) and the heavy chain (30 amino acid differences). As a result of these differences, pertuzumab binds to a completely different epitope on the HER2 receptor. Binding of pertuzumab to the HER2 receptor on human epithelial cells prevents it from forming complexes with other members of the HER receptor family (Agus et al., *Cancer Cell* 2:127-137 (2002)). By blocking complex formation, pertuzumab prevents the growth-stimulatory effects of ligands for the complexes (e.g., EGF and heregulin). In vitro experiments demonstrated that both pertuzumab and pertuzumab-Fab inhibit the binding of heregulin (HRG) to MCF7 cells, and that the HRG-stimulated phosphorylation of the HER2-HER3 complex can be inhibited by both pertuzumab and pertuzumab-Fab (Agus et al., *Cancer Cell* 2:127-137 (2002)). Furthermore, in vivo inhibition of tumor growth by pertuzumab and a polyethylene glycol derivatized Fab of pertuzumab were found to be comparable in a murine prostate cancer xenograft model (Agus et al., *Cancer Cell* 2:127-137 (2002)). These data suggest that the Fc region of the antibody is not necessary for the inhibition of tumor growth, and moreover, bivalency and Fc-mediated effector functions are not required for in vivo or in vitro biological activity.

In this example, the main peak of pertuzumab was collected from a cation exchange column and incubated in cell culture media or processed using standard antibody purification operations. Acidic variants formed upon incubation of main peak with cell culture media components. Acidic variants of monoclonal antibodies are modified forms of the desired product that elute earlier than the main peak upon separation by cation exchange chromatography. Subtle differences in the amount and/or distribution of acidic variants are often observed pre- and post-process changes and pose a challenge to demonstrating product comparability. Purification operations had little effect on formation of acidic variants. Variants identified in the acidic variant fraction included glycated variant, deamidated variant, disulfide-reduced variant, sialylated variant, and non-reducible variant. Collectively, the acidic variants were fully potent.

Amongst other things, the purpose of this study was to: better understand the impact of cell culture and recovery processes on pertuzumab acidic variant formation, characterize the predominant acidic variants of pertuzumab, and evaluate the impact of acidic variants on pharmacokinetics (PK).

Rat pharmacokinetic results show that the area under the curve for the acidic variant fraction and main peak fraction were equivalent to pertuzumab starting material (geometric mean ratios 0.96 and 0.95, respectively). These results demonstrate that although acidic variants are chemically different from the main peak they have equivalent pharmacokinetics.

Methods and Results

Figure 10:
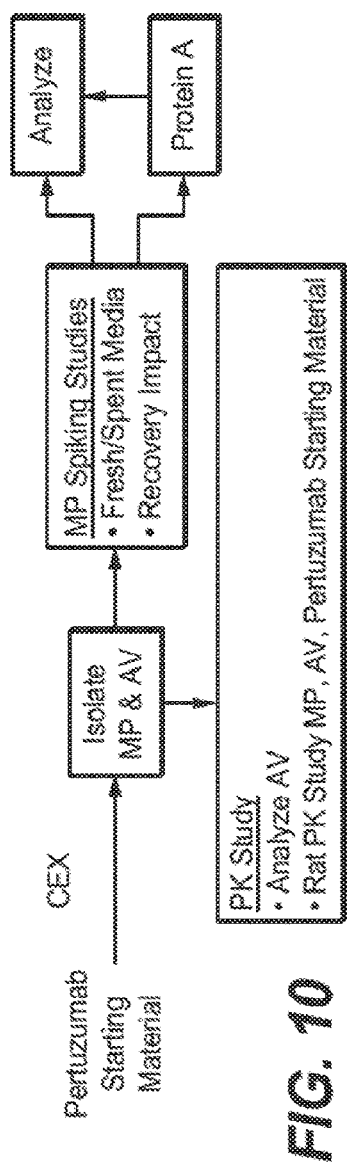
FIG. 10 shows experimental design for isolation of cation exchange MP (Main Peak) and AV (Acidic Variants), cell culture, recovery, and PK (pharmacokinetics) evaluation and analytical testing. Fresh media=standard media; spent media=standard media after 12 days of cell culture, cells were removed by centrifugation. Dissolved oxygen, pH, and other parameters were not controlled.

FIG. 10 depicts the experimental design for isolation of cation exchange MP (Main Peak) and AV (Acidic Variants), cell culture, recovery, and PK (pharmacokinetics) evaluation and analytical testing. Fresh media=standard media; spent media=standard media after 12 days of cell culture, cells were removed by centrifugation. Dissolved oxygen, pH, and other parameters were not controlled.

A. Isolation of Main Peak and Acidic Variants

Figure 11:
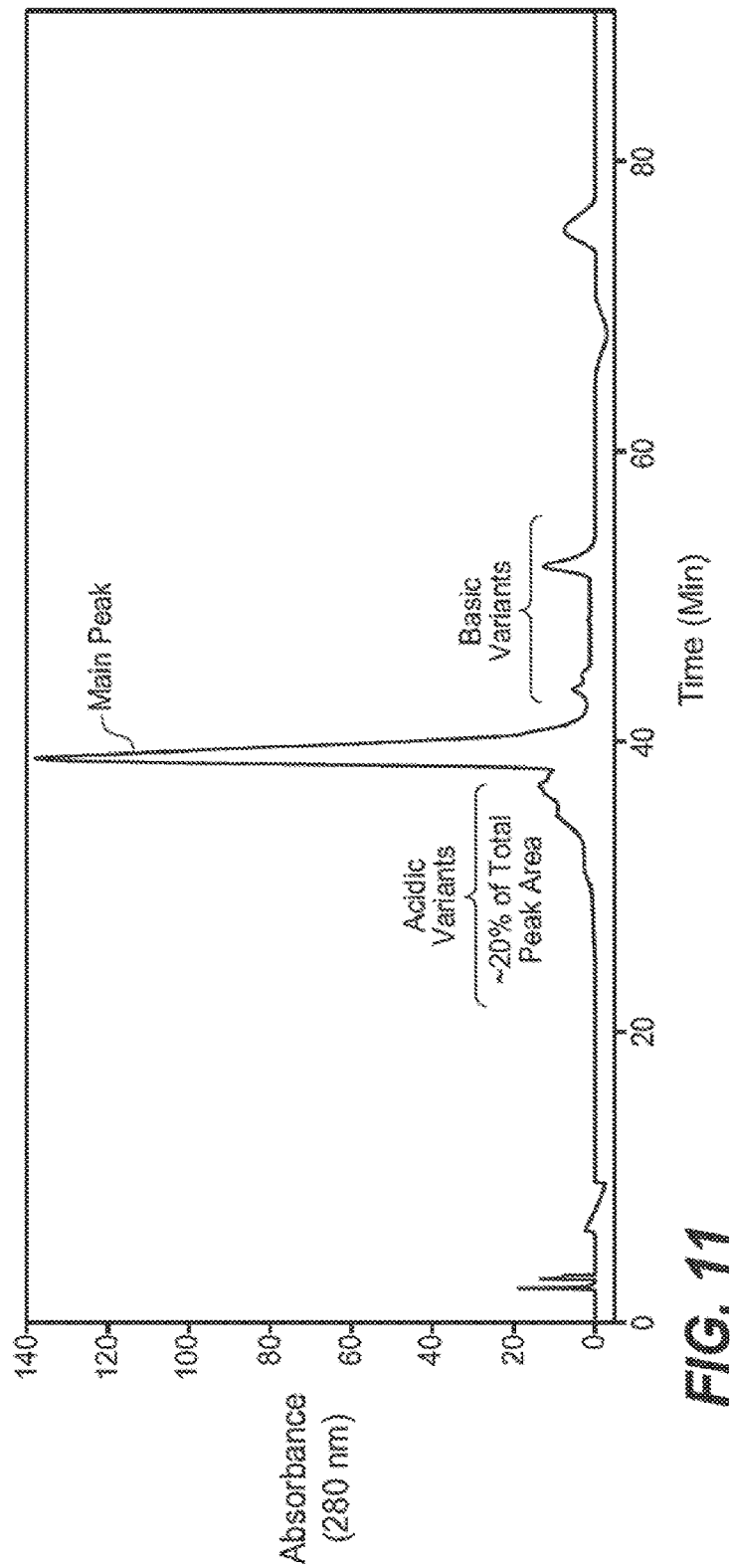
FIG. 11 shows a typical DIONEX PROPAC® cation exchange (CEX) chromatogram from Example 1.

Charge variants of pertuzumab were separated on a 4.0× 250 mm DIONEX PROPAC WCX-10® cation exchange (CEX) column using the following conditions:
Buffer A: 20 mM BisTris, pH 6.0
Buffer B: 20 mM BisTris, 200 mM NaCl, pH 6.0
Gradient: 0.5% B/min delivered at 1.0 mL/min
Column Temperature: 35NC
Detection: 280 nm A typical chromatogram is shown in FIG. 11. AV (acidic variant) and MP (main peak) fractions were collected.

Figures 12, 13:
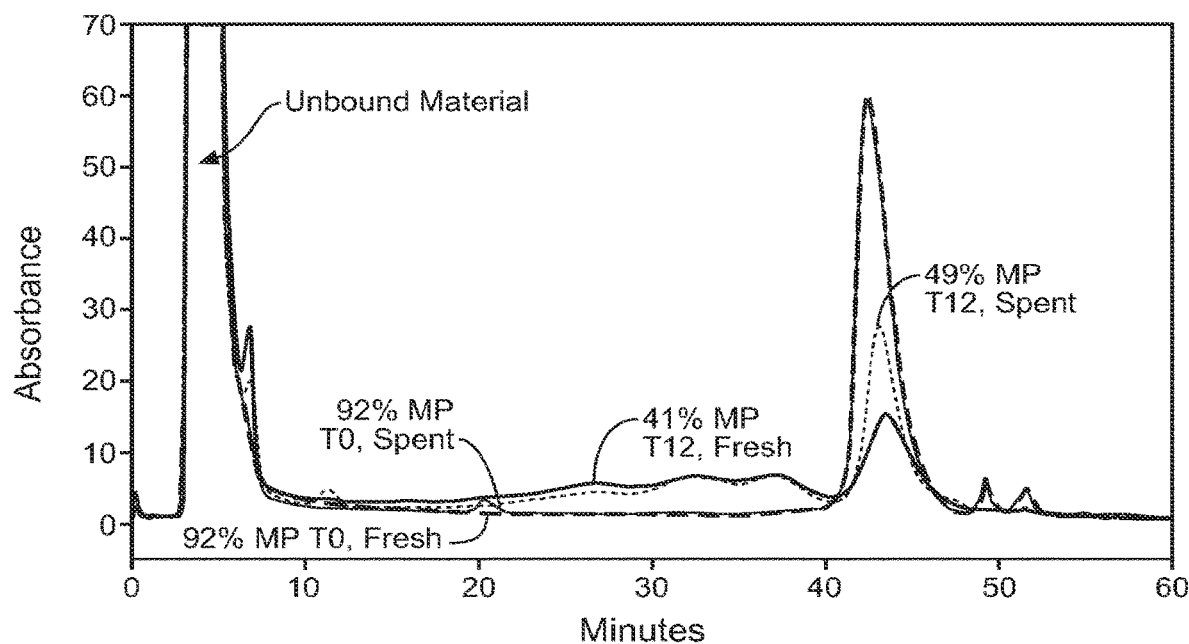
FIG. 12 shows analysis of pertuzumab starting material and CEX fractions. AV=acidic variant; MP=main peak; and BV=basic variant.
FIG. 13 reveals CEX of main peak (MP) spiked into cell culture media and incubated for 12 days.

Potency and monomer content were similar among the pertuzmab starting material, main peak, and acidic variants (FIG. 12). Purity of the main peak and acidic variant CEX fractions was acceptable for pharmacokinetics studies based on the criteria of 90% purity by CEX (FIG. 12).

B. Main Peak Spiking Experiments

Pertuzumab main peak isolated by CEX was spiked into either fresh or spent cell culture media (no cells) and incubated for 12 days at 37NC as outlined in FIG. 10. Samples at various time points were directly analyzed by CEX or after isolation by protein A. Main peak was also spiked into media +/− various media components such as glucose and peptone. In addition, main peak was processed through standard recovery operations such as protein A chromatography (ProA), low pH treatment, and SP SEPHAROSE® Fast Flow (SPFF) for multiple cycles and analyzed by CEX.

CEX profiles of main peak incubated for 12 days in fresh or spent media were similar (FIGS. 13 and 14). Main peak decreased more after incubation in fresh media than in spent media. Removal of various media components did affect the decrease of main peak. Percent main peak in incubated samples was the same with and without protein A isolation. Incubation in media buffer alone caused a loss of main peak.

Protein A isolation of main peak from media did not affect the CEX profile demonstrating that modifications during incubation do not affect protein A binding or elution. Recovery operations had little or no effect on the percent CEX main peak.

C. Characterization of Acidic Variants

Pertuzumab acidic variants were isolated by CEX from pertuzumab starting material or main peak incubated in cell culture media. The isolated acidic variants were analyzed by the methods listed in FIG. 15. Acidic variants comprise 21% of total peak area, therefore about 80% (17% of 21%) of acidic variants were identified. Deamidated forms could not be quantified.

Forms identified in acidic variants generated by main peak incubated with media were the same as those identified in pertuzumab starting material. The following forms were detected: sialylated variant, disulfide reduced variant, glycated variant, non-reducible variant, and deamidated variant. Higher order glycated forms were identified by electrospray ionization-mass spectrometry (ESI-MS) after reduction and PNGase treatment.

D. Pharmacokinetics (PK) Study

Figures 16, 17:
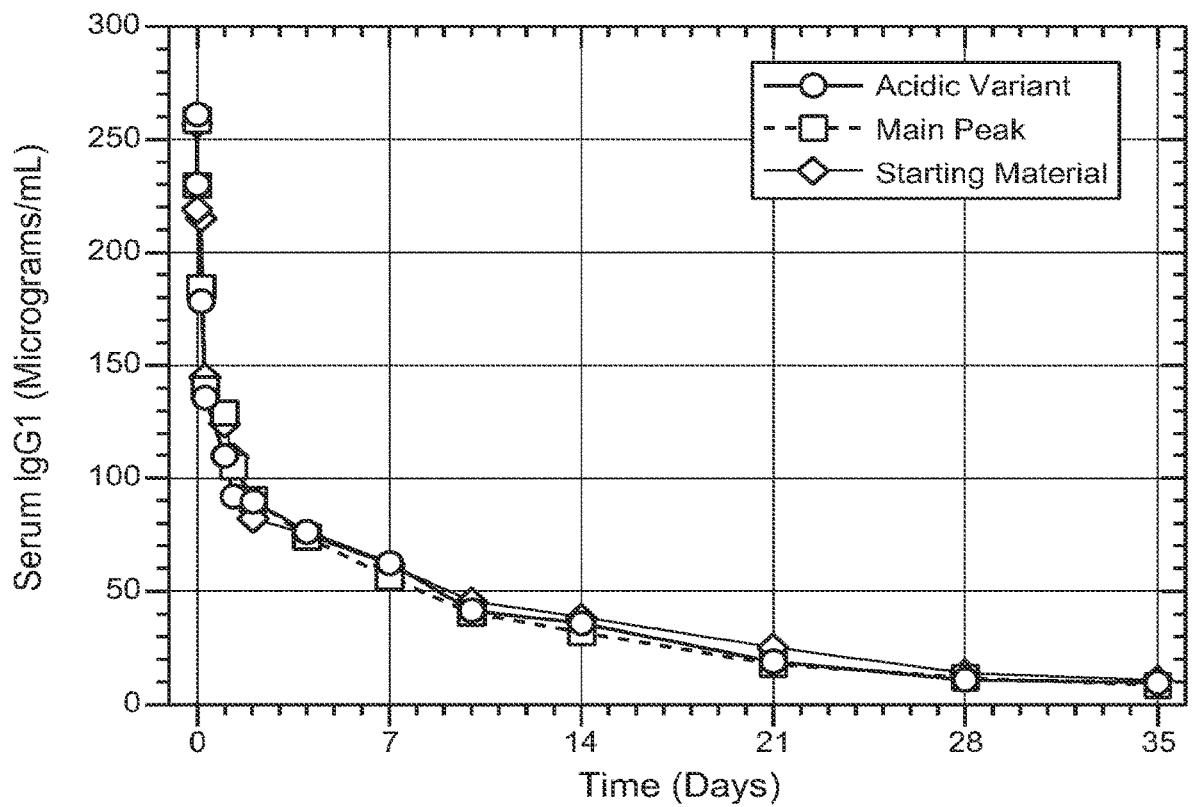
FIG. 16 shows pertuzumab concentration versus time in the PK studies in Example 1.
FIG. 17 provides the area under the curve (AUC) and geometric mean ratios from the PK study in Example 1.

A single intravenous (IV) dose of 10 mg/kg, 12 rats per arm, 3 arms (acidic variants, main peak, pertuzumab starting material). Extensive PK sampling was conducted for 35 days. Geometric Mean Ratio of AUC (Day 0-14) between acidic, main peak, and pertuzumab starting material. Geometric Mean Ratio=GM Sample/GM IgG1 Starting Material. Pertuzumab concentration versus time curve were similar for the pertuzumab starting material, acidic variant, and main peak (FIGS. 16 and 17). No significant difference in exposure was observed between acidic variants, main peak, and pertuzumab starting material. The GMR was ~1.0 with 90% CI between 0.80 B 1.25.

CONCLUSIONS

Multiple cell culture factors contribute to acidic variant formation, but recovery was not shown to effect acidic variant formation. Disulfide reduced, non-reducible, sialylated, glycated, and deamidated variants were identified in the acidic fraction. Acidic fraction isolated from pertuzumab starting material and those generated by incubation of CEX main peak contained the same forms. Acidic variants, main peak, and pertuzumab starting material had the same pharmacokinetics.

---

What is claimed is:

1. A method of making a pharmaceutical composition comprising: (1) preparing a composition comprising a main species HER2 antibody that binds to domain II of HER2 and comprises variable light and variable heavy amino acid sequences set forth in SEQ ID Nos. 3 and 4, respectively, and acidic variants thereof comprising disulfide reduced variant, and (2) determining the acidic variants in the composition, and confirming that the amount thereof is less than about 25%.

2. The method of claim 1 wherein step (2) further comprises identifying the disulfide reduced variant comprised in the acidic variants by non-reduced capillary electrophoresis with sodium dodecyl sulfate (CE-SDS).

3. The method of claim 1 wherein step (2) comprises determining the acidic variants by ion exchange chromatography.

4. The method of claim 3 which comprises cation exchange chromatography using a cation exchanger with a carboxylate functional group.

5. The method of claim 4 wherein the conditions for the chromatography comprise: Buffer A, 20 mM BisTris, pH 6.0; Buffer B, 20 mM BisTris, 200 mM NaCl, pH 6.0; and a gradient of 0.5% Buffer B at 1.0 mL/min.

6. The method of claim 1 comprising combining the composition after step (2) with a pharmaceutically acceptable carrier.

7. The method of claim 1 wherein the composition determined in step (2) is in a pharmaceutically acceptable carrier.

8. The method of claim 1 wherein the acidic variants further comprise glycated variant of the main species antibody.

9. The method of claim 1 wherein the acidic variants further comprise non-reducible variant of the main species antibody.

10. The method of claim 1 wherein the acidic variants further comprise sialylated variant of the main species antibody.

11. The method of claim 1 wherein the acidic variants further comprise deamidated variant of the main species antibody.

12. The method of claim 1 wherein the acidic variants further comprise glycated variant, deamidated variant, sialylated variant, and non-reducible variant of the main species antibody.

13. The method of claim 12 wherein the glycated variant, deamidated variant, disulfide reduced variant, sialylated variant, and non-reducible variant constitute at least 75 to 80% of the acidic variants in the composition.

14. The method of claim 1 wherein the main species HER2 antibody comprises light chain and heavy chain amino acid sequences set forth in SEQ ID Nos. 15 and 16, respectively.

15. The method of claim 1 wherein the disulfide reduced variant has one or more reduced interchain disulfide bonds and is detectable by non-reduced CE-SDS.

16. The method of claim 15 wherein the disulfide reduced variant comprises 1% to 6% of the composition measurable by non-reduced CE-SDS.

17. The method of claim 1 wherein the composition further comprises an amino acid-terminal leader extension of the main species antibody, wherein the amino-terminal leader extension comprises or consists of VHS-.

18. The method of claim 1 wherein the composition further comprises an amino acid sequence variant of the main species HER2 antibody selected from the group consisting of an antibody comprising a C-terminal lysine residue on one or both heavy chains thereof, and an antibody with one or more oxidized methionine residues.

19. The method of claim 1 wherein the composition is expressed by and recovered from a Chinese Hamster Ovary cell line expressing the main species HER2 antibody.

20. A method of making a pharmaceutical composition comprising: (1) preparing a composition comprising a main species HER2 antibody that binds to domain II and comprises light chain and heavy chain amino acid sequences set forth in SEQ ID Nos. 15 and 16, respectively, and acidic variants thereof comprising disulfide reduced variant which has one or more reduced interchain disulfide bonds, and (2) determining acidic variants in the composition, wherein the amount of disulfide reduced variant comprises 1% to 6% of the composition measurable by non-reduced CE-SDS.

21. The method of claim 20 comprising combining the composition after step (2) with a pharmaceutically acceptable carrier.

22. The method of claim 20 wherein the composition determined in step (2) is in a pharmaceutically acceptable carrier.

23. The method of claim 20 wherein the acidic variants further comprise glycated variant of the main species antibody.

24. The method of claim 20 wherein the acidic variants further comprise non-reducible variant of the main species antibody.

25. The method of claim 20 wherein the acidic variants further comprise sialylated variant of the main species antibody.

26. The method of claim 20 wherein the acidic variants further comprise deamidated variant of the main species antibody.

27. The method of claim 20 wherein the acidic variants further comprise glycated variant, deamidated variant, sialylated variant, and non-reducible variant of the main species antibody.

28. The method of claim 27 wherein the glycated variant, deamidated variant, disulfide reduced variant, sialylated variant, and non-reducible variant constitute at least 75 to 80% of the acidic variants in the composition.

29. The method of claim 20 wherein the composition further comprises an amino acid-terminal leader extension of the main species antibody, wherein the amino-terminal leader extension comprises or consists of VHS-.

30. The method of claim 20 wherein the composition further comprises an amino acid sequence variant of the main species HER2 antibody selected from the group consisting of an antibody comprising a C-terminal lysine residue on one or both heavy chains thereof, and an antibody with one or more oxidized methionine residues.

31. The method of claim 20 wherein the composition is expressed by and recovered from a Chinese Hamster Ovary cell line expressing the main species HER2 antibody.

* * * * *

UNITED STATES PATENT AND TRADEMARK OFFICE
CERTIFICATE OF CORRECTION

PATENT NO. : 11,414,498 B2  
APPLICATION NO. : 16/503364  
DATED : August 16, 2022  
INVENTOR(S) : Reed J. Harris et al.

Page 1 of 1

It is certified that error appears in the above-identified patent and that said Letters Patent is hereby corrected as shown below:

On the Title Page

Item (72) Inventors delete "Paul A. Motchnick" and replace with --Paul A. Motchnik--

Signed and Sealed this
Tenth Day of September, 2024

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 107
<212> TYPE: PRT
<213> ORGANISM: Mus musculus

<400> SEQUENCE: 1

Asp Thr Val Met Thr Gln Ser His Lys Ile Met Ser Thr Ser Val
 1               5                  10                  15

Gly Asp Arg Val Ser Ile Thr Cys Lys Ala Ser Gln Asp Val Ser
                20                  25                  30

Ile Gly Val Ala Trp Tyr Gln Gln Arg Pro Gly Gln Ser Pro Lys
                35                  40                  45

Leu Leu Ile Tyr Ser Ala Ser Tyr Arg Tyr Thr Gly Val Pro Asp
                50                  55                  60

Arg Phe Thr Gly Ser Gly Ser Gly Thr Asp Phe Thr Phe Thr Ile
                65                  70                  75

Ser Ser Val Gln Ala Glu Asp Leu Ala Val Tyr Tyr Cys Gln Gln
                80                  85                  90

Tyr Tyr Ile Tyr Pro Tyr Thr Phe Gly Gly Gly Thr Lys Leu Glu
                95                  100                 105

Ile Lys

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Pro Glu Leu Val Lys Pro Gly
 1               5                  10                  15

Thr Ser Val Lys Ile Ser Cys Lys Ala Ser Gly Phe Thr Phe Thr
                20                  25                  30

Asp Tyr Thr Met Asp Trp Val Lys Gln Ser His Gly Lys Ser Leu
                35                  40                  45

Glu Trp Ile Gly Asp Val Asn Pro Asn Ser Gly Gly Ser Ile Tyr
                50                  55                  60

Asn Gln Arg Phe Lys Gly Lys Ala Ser Leu Thr Val Asp Arg Ser
                65                  70                  75

Ser Arg Ile Val Tyr Met Glu Leu Arg Ser Leu Thr Phe Glu Asp
                80                  85                  90

Thr Ala Val Tyr Tyr Cys Ala Arg Asn Leu Gly Pro Ser Phe Tyr
                95                  100                 105

Phe Asp Tyr Trp Gly Gln Gly Thr Thr Leu Thr Val Ser Ser
                110                 115

<210> SEQ ID NO 3
<211> LENGTH: 107
<212> TYPE: PRT
<213> ORGANISM: Artificial Sequence
<220> FEATURE:
<223> OTHER INFORMATION: sequence is synthesized

<400> SEQUENCE: 3

```
Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                 100                 105

Ile Lys
```

<210> SEQ ID NO 4
<211> LENGTH: 119
<212> TYPE: PRT
<213> ORGANISM: Artificial Sequence
<220> FEATURE:
<223> OTHER INFORMATION: sequence is synthesized

<400> SEQUENCE: 4

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
            35                  40                  45

Glu Trp Val Ala Asp Val Asn Pro Asn Ser Gly Gly Ser Ile Tyr
        50                  55                  60

Asn Gln Arg Phe Lys Gly Arg Phe Thr Leu Ser Val Asp Arg Ser
 65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser
            110                 115
```

<210> SEQ ID NO 5
<211> LENGTH: 107
<212> TYPE: PRT
<213> ORGANISM: Artificial Sequence
<220> FEATURE:
<223> OTHER INFORMATION: sequence is synthesized

<400> SEQUENCE: 5

```
Asp Ile Gln Met Thr Gln Ser Pro Ser Ser Leu Ser Ala Ser Val
 1               5                  10                  15
```

```
Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
            95                  100                 105

Ile Lys

<210> SEQ ID NO 6
<211> LENGTH: 119
<212> TYPE: PRT
<213> ORGANISM: Artificial Sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
            35                  40                  45

Glu Trp Val Ala Val Ile Ser Gly Asp Gly Gly Ser Thr Tyr Tyr
        50                  55                  60

Ala Asp Ser Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
            95                  100                 105

Tyr Asp Tyr Trp Gly Gln Gly Thr Leu Val Thr Val Ser Ser
        110                 115

<210> SEQ ID NO 7
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Xaa is preferrably D or S

<400> SEQUENCE: 7

Gly Phe Thr Phe Thr Asp Tyr Thr Met Xaa
                5                   10

<210> SEQ ID NO 8
<211> LENGTH: 17
<212> TYPE: PRT
<213> ORGANISM: Artificial sequence
<220> FEATURE:
<223> OTHER INFORMATION: Sequence is synthesized.
```

<400> SEQUENCE: 8

Asp Val Asn Pro Asn Ser Gly Gly Ser Ile Tyr Asn Gln Arg Phe
 1               5                  10                  15

Lys Gly

<210> SEQ ID NO 9
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 9

Asn Leu Gly Pro Ser Phe Tyr Phe Asp Tyr
                 5                  10

<210> SEQ ID NO 10
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 10

Lys Ala Ser Gln Asp Val Ser Ile Gly Val Ala
                 5                  10

<210> SEQ ID NO 11
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 5
<223> OTHER INFORMATION: Xaa  is preferably R or L
<220> FEATURE:
<221> NAME/KEY: Xaa
<222> LOCATION: 6
<223> OTHER INFORMATION: Xaa is  preferably Y or E
<220> FEATURE:
<221> NAME/KEY: Xaa
<222> LOCATION: 7
<223> OTHER INFORMATION: Xaa is preferably T or S

<400> SEQUENCE: 11

Ser Ala Ser Tyr Xaa Xaa Xaa
                 5

<210> SEQ ID NO 12
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 12

Gln Gln Tyr Tyr Ile Tyr Pro Tyr Thr
                 5

<210> SEQ ID NO 13
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 13

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys
```

<210> SEQ ID NO 14
<211> LENGTH: 449
<212> TYPE: PRT
<213> ORGANISM: Artificial sequence
<220> FEATURE:
<223> OTHER INFORMATION: sequence is synthesized

<400> SEQUENCE: 14

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                 100                 105

Ala Met Asp Tyr Trp Gly Gln Gly Thr Leu Val Thr Val Ser Ser
```

```
                    110                 115                 120
Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
                155                 160                 165

Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp
                305                 310                 315

Trp Leu Asn Gly Lys Glu Tyr Lys Cys Lys Val Ser Asn Lys Ala
                320                 325                 330

Leu Pro Ala Pro Ile Glu Lys Thr Ile Ser Lys Ala Lys Gly Gln
                335                 340                 345

Pro Arg Glu Pro Gln Val Tyr Thr Leu Pro Pro Ser Arg Glu Glu
                350                 355                 360

Met Thr Lys Asn Gln Val Ser Leu Thr Cys Leu Val Lys Gly Phe
                365                 370                 375

Tyr Pro Ser Asp Ile Ala Val Glu Trp Glu Ser Asn Gly Gln Pro
                380                 385                 390

Glu Asn Asn Tyr Lys Thr Thr Pro Pro Val Leu Asp Ser Asp Gly
                395                 400                 405

Ser Phe Phe Leu Tyr Ser Lys Leu Thr Val Asp Lys Ser Arg Trp
                410                 415                 420

Gln Gln Gly Asn Val Phe Ser Cys Ser Val Met His Glu Ala Leu
                425                 430                 435

His Asn His Tyr Thr Gln Lys Ser Leu Ser Leu Ser Pro Gly
                440                 445

<210> SEQ ID NO 15
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 15

Asp Ile Gln Met Thr Gln Ser Pro Ser Ser Leu Ser Ala Ser Val
```

```
              1               5                  10                 15
            Gly Asp Arg Val Thr Ile Thr Cys Lys Ala Ser Gln Asp Val Ser
                              20                 25                 30
            Ile Gly Val Ala Trp Tyr Gln Gln Lys Pro Gly Lys Ala Pro Lys
                              35                 40                 45
            Leu Leu Ile Tyr Ser Ala Ser Tyr Arg Tyr Thr Gly Val Pro Ser
                              50                 55                 60
            Arg Phe Ser Gly Ser Gly Ser Gly Thr Asp Phe Thr Leu Thr Ile
                              65                 70                 75
            Ser Ser Leu Gln Pro Glu Asp Phe Ala Thr Tyr Tyr Cys Gln Gln
                              80                 85                 90
            Tyr Tyr Ile Tyr Pro Tyr Thr Phe Gly Gln Gly Thr Lys Val Glu
                              95                 100                105
            Ile Lys Arg Thr Val Ala Ala Pro Ser Val Phe Ile Phe Pro Pro
                              110                115                120
            Ser Asp Glu Gln Leu Lys Ser Gly Thr Ala Ser Val Val Cys Leu
                              125                130                135
            Leu Asn Asn Phe Tyr Pro Arg Glu Ala Lys Val Gln Trp Lys Val
                              140                145                150
            Asp Asn Ala Leu Gln Ser Gly Asn Ser Gln Glu Ser Val Thr Glu
                              155                160                165
            Gln Asp Ser Lys Asp Ser Thr Tyr Ser Leu Ser Ser Thr Leu Thr
                              170                175                180
            Leu Ser Lys Ala Asp Tyr Glu Lys His Lys Val Tyr Ala Cys Glu
                              185                190                195
            Val Thr His Gln Gly Leu Ser Ser Pro Val Thr Lys Ser Phe Asn
                              200                205                210
            Arg Gly Glu Cys

<210> SEQ ID NO 16
<211> LENGTH: 448
<212> TYPE: PRT
<213> ORGANISM: Artificial sequence
<220> FEATURE:
<223> OTHER INFORMATION: Sequence is synthesized.

<400> SEQUENCE: 16

Glu Val Gln Leu Val Glu Ser Gly Gly Gly Leu Val Gln Pro Gly
              1               5                  10                 15
            Gly Ser Leu Arg Leu Ser Cys Ala Ala Ser Gly Phe Thr Phe Thr
                              20                 25                 30
            Asp Tyr Thr Met Asp Trp Val Arg Gln Ala Pro Gly Lys Gly Leu
                              35                 40                 45
            Glu Trp Val Ala Asp Val Asn Pro Asn Ser Gly Gly Ser Ile Tyr
                              50                 55                 60
            Asn Gln Arg Phe Lys Gly Arg Phe Thr Leu Ser Val Asp Arg Ser
                              65                 70                 75
            Lys Asn Thr Leu Tyr Leu Gln Met Asn Ser Leu Arg Ala Glu Asp
                              80                 85                 90
            Thr Ala Val Tyr Tyr Cys Ala Arg Asn Leu Gly Pro Ser Phe Tyr
                              95                 100                105
            Phe Asp Tyr Trp Gly Gln Gly Thr Leu Val Thr Val Ser Ser Ala
                              110                115                120
            Ser Thr Lys Gly Pro Ser Val Phe Pro Leu Ala Pro Ser Ser Lys
                              125                130                135
```

```
Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445

<210> SEQ ID NO 17
<211> LENGTH: 233
<212> TYPE: PRT
<213> ORGANISM: Artificial sequence
<220> FEATURE:
<223> OTHER INFORMATION: Sequence is synthesized.

<400> SEQUENCE: 17

Met Gly Trp Ser Cys Ile Ile Leu Phe Leu Val Ala Thr Ala Thr
  1               5                  10                  15

Gly Val His Ser Asp Ile Gln Met Thr Gln Ser Pro Ser Ser Leu
             20                  25                  30
```

Ser Ala Ser Val Gly Asp Arg Val Thr Ile Thr Cys Lys Ala Ser
                35                  40                  45

Gln Asp Val Ser Ile Gly Val Ala Trp Tyr Gln Gln Lys Pro Gly
            50                  55                  60

Lys Ala Pro Lys Leu Leu Ile Tyr Ser Ala Ser Tyr Arg Tyr Thr
        65                  70                  75

Gly Val Pro Ser Arg Phe Ser Gly Ser Gly Ser Gly Thr Asp Phe
    80                  85                  90

Thr Leu Thr Ile Ser Ser Leu Gln Pro Glu Asp Phe Ala Thr Tyr
95                  100                 105

Tyr Cys Gln Gln Tyr Tyr Ile Tyr Pro Tyr Thr Phe Gly Gln Gly
                110                 115                 120

Thr Lys Val Glu Ile Lys Arg Thr Val Ala Ala Pro Ser Val Phe
            125                 130                 135

Ile Phe Pro Pro Ser Asp Glu Gln Leu Lys Ser Gly Thr Ala Ser
        140                 145                 150

Val Val Cys Leu Leu Asn Asn Phe Tyr Pro Arg Glu Ala Lys Val
    155                 160                 165

Gln Trp Lys Val Asp Asn Ala Leu Gln Ser Gly Asn Ser Gln Glu
170                 175                 180

Ser Val Thr Glu Gln Asp Ser Lys Asp Ser Thr Tyr Ser Leu Ser
                185                 190                 195

Ser Thr Leu Thr Leu Ser Lys Ala Asp Tyr Glu Lys His Lys Val
            200                 205                 210

Tyr Ala Cys Glu Val Thr His Gln Gly Leu Ser Ser Pro Val Thr
        215                 220                 225

Lys Ser Phe Asn Arg Gly Glu Cys
    230

<210> SEQ ID NO 18
<211> LENGTH: 467
<212> TYPE: PRT
<213> ORGANISM: Artificial sequence
<220> FEATURE:
<223> OTHER INFORMATION: Sequence is synthesized.

<400> SEQUENCE: 18

Met Gly Trp Ser Cys Ile Ile Leu Phe Leu Val Ala Thr Ala Thr
1               5                   10                  15

Gly Val His Ser Glu Val Gln Leu Val Glu Ser Gly Gly Gly Leu
            20                  25                  30

Val Gln Pro Gly Gly Ser Leu Arg Leu Ser Cys Ala Ala Ser Gly
        35                  40                  45

Phe Thr Phe Thr Asp Tyr Thr Met Asp Trp Val Arg Gln Ala Pro
    50                  55                  60

Gly Lys Gly Leu Glu Trp Val Ala Asp Val Asn Pro Asn Ser Gly
65                  70                  75

Gly Ser Ile Tyr Asn Gln Arg Phe Lys Gly Arg Phe Thr Leu Ser
                80                  85                  90

Val Asp Arg Ser Lys Asn Thr Leu Tyr Leu Gln Met Asn Ser Leu
            95                  100                 105

Arg Ala Glu Asp Thr Ala Val Tyr Tyr Cys Ala Arg Asn Leu Gly
        110                 115                 120

Pro Ser Phe Tyr Phe Asp Tyr Trp Gly Gln Gly Thr Leu Val Thr
    125                 130                 135

Val Ser Ser Ala Ser Thr Lys Gly Pro Ser Val Phe Pro Leu Ala
            140                 145                 150

Pro Ser Ser Lys Ser Thr Ser Gly Gly Thr Ala Ala Leu Gly Cys
            155                 160                 165

Leu Val Lys Asp Tyr Phe Pro Glu Pro Val Thr Val Ser Trp Asn
            170                 175                 180

Ser Gly Ala Leu Thr Ser Gly Val His Thr Phe Pro Ala Val Leu
            185                 190                 195

Gln Ser Ser Gly Leu Tyr Ser Leu Ser Ser Val Val Thr Val Pro
            200                 205                 210

Ser Ser Ser Leu Gly Thr Gln Thr Tyr Ile Cys Asn Val Asn His
            215                 220                 225

Lys Pro Ser Asn Thr Lys Val Asp Lys Lys Val Glu Pro Lys Ser
            230                 235                 240

Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu
            305                 310                 315

Gln Tyr Asn Ser Thr Tyr Arg Val Val Ser Val Leu Thr Val Leu
            320                 325                 330

His Gln Asp Trp Leu Asn Gly Lys Glu Tyr Lys Cys Lys Val Ser
            335                 340                 345

Asn Lys Ala Leu Pro Ala Pro Ile Glu Lys Thr Ile Ser Lys Ala
            350                 355                 360

Lys Gly Gln Pro Arg Glu Pro Gln Val Tyr Thr Leu Pro Pro Ser
            365                 370                 375

Arg Glu Glu Met Thr Lys Asn Gln Val Ser Leu Thr Cys Leu Val
            380                 385                 390

Lys Gly Phe Tyr Pro Ser Asp Ile Ala Val Glu Trp Glu Ser Asn
            395                 400                 405

Gly Gln Pro Glu Asn Asn Tyr Lys Thr Thr Pro Pro Val Leu Asp
            410                 415                 420

Ser Asp Gly Ser Phe Phe Leu Tyr Ser Lys Leu Thr Val Asp Lys
            425                 430                 435

Ser Arg Trp Gln Gln Gly Asn Val Phe Ser Cys Ser Val Met His
            440                 445                 450

Glu Ala Leu His Asn His Tyr Thr Gln Lys Ser Leu Ser Leu Ser
            455                 460                 465

Pro Gly

<210> SEQ ID NO 19
<211> LENGTH: 195
<212> TYPE: PRT
<213> ORGANISM: Homo sapiens

<400> SEQUENCE: 19

Thr Gln Val Cys Thr Gly Thr Asp Met Lys Leu Arg Leu Pro Ala
  1               5                  10                  15

-continued

```
Ser Pro Glu Thr His Leu Asp Met Leu Arg His Leu Tyr Gln Gly
             20                  25                  30

Cys Gln Val Val Gln Gly Asn Leu Glu Leu Thr Tyr Leu Pro Thr
             35                  40                  45

Asn Ala Ser Leu Ser Phe Leu Gln Asp Ile Gln Glu Val Gln Gly
             50                  55                  60

Tyr Val Leu Ile Ala His Asn Gln Val Arg Gln Val Pro Leu Gln
             65                  70                  75

Arg Leu Arg Ile Val Arg Gly Thr Gln Leu Phe Glu Asp Asn Tyr
             80                  85                  90

Ala Leu Ala Val Leu Asp Asn Gly Asp Pro Leu Asn Asn Thr Thr
             95                 100                 105

Pro Val Thr Gly Ala Ser Pro Gly Gly Leu Arg Glu Leu Gln Leu
            110                 115                 120

Arg Ser Leu Thr Glu Ile Leu Lys Gly Gly Val Leu Ile Gln Arg
            125                 130                 135

Asn Pro Gln Leu Cys Tyr Gln Asp Thr Ile Leu Trp Lys Asp Ile
            140                 145                 150

Phe His Lys Asn Asn Gln Leu Ala Leu Thr Leu Ile Asp Thr Asn
            155                 160                 165

Arg Ser Arg Ala Cys His Pro Cys Ser Pro Met Cys Lys Gly Ser
            170                 175                 180

Arg Cys Trp Gly Glu Ser Ser Glu Asp Cys Gln Ser Leu Thr Arg
            185                 190                 195
```

<210> SEQ ID NO 20
<211> LENGTH: 124
<212> TYPE: PRT
<213> ORGANISM: Homo sapiens

<400> SEQUENCE: 20

```
Thr Val Cys Ala Gly Gly Cys Ala Arg Cys Lys Gly Pro Leu Pro
  1               5                  10                  15

Thr Asp Cys Cys His Glu Gln Cys Ala Ala Gly Cys Thr Gly Pro
             20                  25                  30

Lys His Ser Asp Cys Leu Ala Cys Leu His Phe Asn His Ser Gly
             35                  40                  45

Ile Cys Glu Leu His Cys Pro Ala Leu Val Thr Tyr Asn Thr Asp
             50                  55                  60

Thr Phe Glu Ser Met Pro Asn Pro Glu Gly Arg Tyr Thr Phe Gly
             65                  70                  75

Ala Ser Cys Val Thr Ala Cys Pro Tyr Asn Tyr Leu Ser Thr Asp
             80                  85                  90

Val Gly Ser Cys Thr Leu Val Cys Pro Leu His Asn Gln Glu Val
             95                 100                 105

Thr Ala Glu Asp Gly Thr Gln Arg Cys Glu Lys Cys Ser Lys Pro
            110                 115                 120

Cys Ala Arg Val
```

<210> SEQ ID NO 21
<211> LENGTH: 169
<212> TYPE: PRT
<213> ORGANISM: Homo sapiens

<400> SEQUENCE: 21

Cys Tyr Gly Leu Gly Met Glu His Leu Arg Glu Val Arg Ala Val
1               5                   10                  15

Thr Ser Ala Asn Ile Gln Glu Phe Ala Gly Cys Lys Lys Ile Phe
            20                  25                  30

Gly Ser Leu Ala Phe Leu Pro Glu Ser Phe Asp Gly Asp Pro Ala
            35                  40                  45

Ser Asn Thr Ala Pro Leu Gln Pro Glu Gln Leu Gln Val Phe Glu
            50                  55                  60

Thr Leu Glu Glu Ile Thr Gly Tyr Leu Tyr Ile Ser Ala Trp Pro
            65                  70                  75

Asp Ser Leu Pro Asp Leu Ser Val Phe Gln Asn Leu Gln Val Ile
            80                  85                  90

Arg Gly Arg Ile Leu His Asn Gly Ala Tyr Ser Leu Thr Leu Gln
            95                  100                 105

Gly Leu Gly Ile Ser Trp Leu Gly Leu Arg Ser Leu Arg Glu Leu
            110                 115                 120

Gly Ser Gly Leu Ala Leu Ile His His Asn Thr His Leu Cys Phe
            125                 130                 135

Val His Thr Val Pro Trp Asp Gln Leu Phe Arg Asn Pro His Gln
            140                 145                 150

Ala Leu Leu His Thr Ala Asn Arg Pro Glu Asp Glu Cys Val Gly
            155                 160                 165

Glu Gly Leu Ala

<210> SEQ ID NO 22
<211> LENGTH: 142
<212> TYPE: PRT
<213> ORGANISM: Homo sapiens

<400> SEQUENCE: 22

Cys His Gln Leu Cys Ala Arg Gly His Cys Trp Gly Pro Gly Pro
1               5                   10                  15

Thr Gln Cys Val Asn Cys Ser Gln Phe Leu Arg Gly Gln Glu Cys
            20                  25                  30

Val Glu Glu Cys Arg Val Leu Gln Gly Leu Pro Arg Glu Tyr Val
            35                  40                  45

Asn Ala Arg His Cys Leu Pro Cys His Pro Glu Cys Gln Pro Gln
            50                  55                  60

Asn Gly Ser Val Thr Cys Phe Gly Pro Glu Ala Asp Gln Cys Val
            65                  70                  75

Ala Cys Ala His Tyr Lys Asp Pro Pro Phe Cys Val Ala Arg Cys
            80                  85                  90

Pro Ser Gly Val Lys Pro Asp Leu Ser Tyr Met Pro Ile Trp Lys
            95                  100                 105

Phe Pro Asp Glu Glu Gly Ala Cys Gln Pro Cys Pro Ile Asn Cys
            110                 115                 120

Thr His Ser Cys Val Asp Leu Asp Asp Lys Gly Cys Pro Ala Glu
            125                 130                 135

Gln Arg Ala Ser Pro Leu Thr
            140

<210> SEQ ID NO 23
<211> LENGTH: 217
<212> TYPE: PRT
<213> ORGANISM: Artificial sequence
<220> FEATURE:

<223> OTHER INFORMATION: Sequence is synthesized.

<400> SEQUENCE: 23

```
Val His Ser Asp Ile Gln Met Thr Gln Ser Pro Ser Ser Leu Ser
 1               5                  10                  15

Ala Ser Val Gly Asp Arg Val Thr Ile Thr Cys Lys Ala Ser Gln
                20                  25                  30

Asp Val Ser Ile Gly Val Ala Trp Tyr Gln Gln Lys Pro Gly Lys
                35                  40                  45

Ala Pro Lys Leu Leu Ile Tyr Ser Ala Ser Tyr Arg Tyr Thr Gly
                50                  55                  60

Val Pro Ser Arg Phe Ser Gly Ser Gly Ser Gly Thr Asp Phe Thr
                65                  70                  75

Leu Thr Ile Ser Ser Leu Gln Pro Glu Asp Phe Ala Thr Tyr Tyr
                80                  85                  90

Cys Gln Gln Tyr Tyr Ile Tyr Pro Tyr Thr Phe Gly Gln Gly Thr
                95                 100                 105

Lys Val Glu Ile Lys Arg Thr Val Ala Ala Pro Ser Val Phe Ile
               110                 115                 120

Phe Pro Pro Ser Asp Glu Gln Leu Lys Ser Gly Thr Ala Ser Val
               125                 130                 135

Val Cys Leu Leu Asn Asn Phe Tyr Pro Arg Glu Ala Lys Val Gln
               140                 145                 150

Trp Lys Val Asp Asn Ala Leu Gln Ser Gly Asn Ser Gln Glu Ser
               155                 160                 165

Val Thr Glu Gln Asp Ser Lys Asp Ser Thr Tyr Ser Leu Ser Ser
               170                 175                 180

Thr Leu Thr Leu Ser Lys Ala Asp Tyr Glu Lys His Lys Val Tyr
               185                 190                 195

Ala Cys Glu Val Thr His Gln Gly Leu Ser Ser Pro Val Thr Lys
               200                 205                 210

Ser Phe Asn Arg Gly Glu Cys
               215
```

<210> SEQ ID NO 24
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 24

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
                35                  40                  45

Glu Trp Val Ala Asp Val Asn Pro Asn Ser Gly Gly Ser Ile Tyr
                50                  55                  60

Asn Gln Arg Phe Lys Gly Arg Phe Thr Leu Ser Val Asp Arg Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105
```

```
Phe Asp Tyr Trp Gly Gln Gly Thr Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly Lys
            440                 445
```